United States Patent
Caponigro et al.

(10) Patent No.: US 12,011,449 B2
(45) Date of Patent: *Jun. 18, 2024

(54) THERAPEUTIC COMBINATIONS COMPRISING A C-RAF INHIBITOR

(71) Applicant: Novartis AG, Basel (CH)

(72) Inventors: Giordano Caponigro, Foxborough, MA (US); Vesselina Cooke, Newton, MA (US); Matthew John Meyer, Framingham, MA (US); Darrin Stuart, Marblehead, MA (US)

(73) Assignee: NOVARTIS AG, Basel (CH)

( * ) Notice: Subject to any disclaimer, the term of this patent is extended or adjusted under 35 U.S.C. 154(b) by 660 days.

This patent is subject to a terminal disclaimer.

(21) Appl. No.: 17/191,205

(22) Filed: Mar. 3, 2021

(65) Prior Publication Data

US 2022/0008426 A1 Jan. 13, 2022

Related U.S. Application Data

(63) Continuation of application No. 16/332,120, filed as application No. PCT/IB2017/055641 on Sep. 18, 2017, now Pat. No. 10,973,829.

(Continued)

(51) Int. Cl.
*A61K 31/5377* (2006.01)
*A61K 31/4965* (2006.01)
*A61P 35/00* (2006.01)

(52) U.S. Cl.
CPC ...... *A61K 31/5377* (2013.01); *A61K 31/4965* (2013.01); *A61P 35/00* (2018.01)

(58) Field of Classification Search
CPC .. A61K 31/5377; A61K 31/4965; A61P 35/00
See application file for complete search history.

(56) References Cited

U.S. PATENT DOCUMENTS 3,707,475 A   12/1972   Lombardino
5,717,100 A   2/1998   Selnick et al.
(Continued)

FOREIGN PATENT DOCUMENTS

DE   2155558 A1   6/1972
DE   3029376 A1   3/1982
(Continued)

OTHER PUBLICATIONS

Hobbs et al. J Cell Sci (2016) 129 (7): 1287-1292. (Year: 2016).*
(Continued)

*Primary Examiner* — Matthew P Coughlin
*Assistant Examiner* — Ashli Ariana Chicks
(74) *Attorney, Agent, or Firm* — WILSON SONSINI GOODRICH & ROSATI

(57) ABSTRACT

The present invention relates to a combination treatment which comprises (a) at least one ERK inhibitor preferably Compound B as described herein, and (b) a c-RAF inhibitor or a pharmaceutically acceptable salt thereof, preferably Compound A, which may be combined into a single pharmaceutical composition or prepared for separate or sequential administration. It includes a c-RAF inhibitor and an ERK inhibitor prepared for simultaneous, separate or sequential administration for the treatment of a proliferative disease, particularly an advanced solid tumor that harbors a Mitogen-activated protein kinase (MAPK) alteration, and includes methods of using these compounds in combination as well as a commercial package comprising such combination.

8 Claims, 3 Drawing Sheets

Related U.S. Application Data

(60) Provisional application No. 62/396,504, filed on Sep. 19, 2016.

(56) References Cited

U.S. PATENT DOCUMENTS

| | | | |
|---|---|---|---|
| 6,211,177 | B1 | 4/2001 | Sperl et al. |
| 6,248,771 | B1 | 6/2001 | Shenoy et al. |
| 6,268,391 | B1 | 7/2001 | Dickerson et al. |
| 6,358,932 | B1 | 3/2002 | Monia |
| 6,399,603 | B1 | 6/2002 | Jacobs et al. |
| 6,417,194 | B1 | 7/2002 | Fox et al. |
| 6,458,813 | B1 | 10/2002 | Mantlo et al. |
| 6,465,493 | B1 | 10/2002 | Burgess et al. |
| 6,608,053 | B2 | 8/2003 | Hayakawa et al. |
| 7,071,216 | B2 | 7/2006 | Renhowe et al. |
| 7,423,150 | B2 | 9/2008 | Costales et al. |
| 7,531,553 | B2 | 5/2009 | Di Pietro et al. |
| 8,129,394 | B2 | 3/2012 | Hunag et al. |
| 8,242,260 | B2 | 8/2012 | Costales et al. |
| 8,299,108 | B2 | 10/2012 | Amiri et al. |
| 8,415,382 | B2 | 4/2013 | Costales et al. |
| 8,563,553 | B2 | 10/2013 | Costales et al. |
| 9,242,969 | B2 | 1/2016 | Barsanti et al. |
| 9,474,754 | B2 | 10/2016 | Caponigro et al. |
| 9,694,016 | B2 | 7/2017 | Aversa et al. |
| 9,700,557 | B2 | 7/2017 | Caponigro et al. |
| 9,867,825 | B2 | 1/2018 | Caponigro et al. |
| 9,913,844 | B2 | 3/2018 | Caponigro et al. |
| 10,245,267 | B2 | 4/2019 | Aversa et al. |
| 10,328,066 | B2 | 6/2019 | Caponigro et al. |
| 10,485,788 | B2 | 11/2019 | Caponigro et al. |
| 10,548,894 | B2 | 2/2020 | Caponigro et al. |
| 10,709,712 | B2 | 7/2020 | Aversa et al. |
| 10,973,829 | B2 * | 4/2021 | Caponigro ........... A61K 31/505 |
| 11,266,653 | B2 | 3/2022 | Cooke |
| 2001/0014679 | A1 | 8/2001 | Tang et al. |
| 2002/0151544 | A1 | 10/2002 | Hayakawa et al. |
| 2003/0166633 | A1 | 9/2003 | Gaster et al. |
| 2004/0053973 | A1 | 3/2004 | Ohkawa et al. |
| 2004/0063946 | A1 | 4/2004 | Ohkawa et al. |
| 2004/0087626 | A1 | 5/2004 | Renhowe et al. |
| 2004/0122237 | A1 | 6/2004 | Amiri et al. |
| 2005/0192287 | A1 | 9/2005 | Costales et al. |
| 2005/0282805 | A1 | 12/2005 | Hangeland et al. |
| 2008/0051401 | A1 | 2/2008 | Pass |
| 2009/0005359 | A1 | 1/2009 | Cossrow et al. |
| 2009/0298815 | A1 | 12/2009 | Adams et al. |
| 2010/0069629 | A1 | 3/2010 | Shimma et al. |
| 2013/0096149 | A1 | 4/2013 | Madera et al. |
| 2013/0165456 | A1 | 6/2013 | Gilmer et al. |
| 2013/0210818 | A1 | 8/2013 | Huang et al. |
| 2013/0217698 | A1 | 8/2013 | Calienni et al. |
| 2013/0224195 | A1 | 8/2013 | Costales et al. |
| 2014/0011825 | A1 | 1/2014 | Costales et al. |
| 2014/0178360 | A1 | 6/2014 | Kuo et al. |
| 2014/0275003 | A1 | 9/2014 | Barsanti et al. |
| 2015/0216868 | A1 | 8/2015 | Laquerre et al. |
| 2016/0038504 | A1 | 2/2016 | Aversa et al. |
| 2016/0075727 | A1 | 3/2016 | Burger et al. |
| 2017/0202842 | A1 | 7/2017 | Laquerre et al. |
| 2017/0260207 | A1 | 9/2017 | Aversa et al. |
| 2019/0022243 | A1 | 1/2019 | Boshuizen et al. |
| 2022/0143036 | A1 | 5/2022 | Cooke |
| 2022/0267299 | A1 | 8/2022 | Harlacher et al. |

FOREIGN PATENT DOCUMENTS

| | | |
|---|---|---|
| EP | 0149884 B1 | 12/1992 |
| EP | 1232153 B1 | 11/2004 |
| EP | 1721905 A1 | 11/2006 |
| GB | 2306108 A | 4/1997 |
| JP | H02188579 A | 7/1990 |
| JP | H03157383 A | 7/1991 |
| JP | 2000302680 A | 10/2000 |
| JP | 2007246520 A | 9/2007 |
| WO | WO-9808845 A1 | 3/1998 |
| WO | WO-0042012 A1 | 7/2000 |
| WO | WO-0059506 A1 | 10/2000 |
| WO | WO-0062778 A1 | 10/2000 |
| WO | WO-0138324 A2 | 5/2001 |
| WO | WO-0152845 A1 | 7/2001 |
| WO | WO-0152846 A1 | 7/2001 |
| WO | WO-0162756 A1 | 8/2001 |
| WO | WO-0166539 A1 | 9/2001 |
| WO | WO-0166540 A1 | 9/2001 |
| WO | WO-0172737 A1 | 10/2001 |
| WO | WO-0196308 A1 | 12/2001 |
| WO | WO-0206213 A2 | 1/2002 |
| WO | WO-0239954 A2 | 5/2002 |
| WO | WO-0242273 A2 | 5/2002 |
| WO | WO-0244156 A2 | 6/2002 |
| WO | WO-02064136 A2 | 8/2002 |
| WO | WO-02076960 A1 | 10/2002 |
| WO | WO-02094808 A1 | 11/2002 |
| WO | WO-03047577 A2 | 6/2003 |
| WO | WO-03082272 A1 | 10/2003 |
| WO | WO-03087304 A2 | 10/2003 |
| WO | WO-2004002948 A1 | 1/2004 |
| WO | WO-2004026859 A1 | 4/2004 |
| WO | WO-2004026863 A1 | 4/2004 |
| WO | WO-2004085425 A1 | 10/2004 |
| WO | WO-2005028444 A1 | 3/2005 |
| WO | WO-2005034869 A2 | 4/2005 |
| WO | WO-2005047266 A1 | 5/2005 |
| WO | WO-2005103028 A1 | 11/2005 |
| WO | WO-2005105814 A1 | 11/2005 |
| WO | WO-2005116000 A1 | 12/2005 |
| WO | WO-2005121142 A1 | 12/2005 |
| WO | WO-2005123050 A2 | 12/2005 |
| WO | WO-2006005914 A1 | 1/2006 |
| WO | WO-2006005915 A1 | 1/2006 |
| WO | WO-2006005918 A1 | 1/2006 |
| WO | WO-2006026306 A1 | 3/2006 |
| WO | WO-2006038734 A1 | 4/2006 |
| WO | WO-2006044509 A2 | 4/2006 |
| WO | WO-2007118149 A2 | 10/2007 |
| WO | WO-2008018426 A1 | 2/2008 |
| WO | WO-2008071605 A2 | 6/2008 |
| WO | WO-2009001132 A1 | 12/2008 |
| WO | WO-2009003998 A2 | 1/2009 |
| WO | WO-2009006389 A2 | 1/2009 |
| WO | WO-2009007749 A2 | 1/2009 |
| WO | WO-2009012283 A1 | 1/2009 |
| WO | WO-2009014637 A2 | 1/2009 |
| WO | WO-2009030952 A2 | 3/2009 |
| WO | WO-2009032667 A1 | 3/2009 |
| WO | WO-2009047163 A1 | 4/2009 |
| WO | WO-2009106885 A1 | 9/2009 |
| WO | WO-2009115572 A2 | 9/2009 |
| WO | WO-2009137391 A2 | 11/2009 |
| WO | WO-2009152356 A2 | 12/2009 |
| WO | WO-2010010154 A1 | 1/2010 |
| WO | WO-2010020675 A1 | 2/2010 |
| WO | WO-2010048149 A2 | 4/2010 |
| WO | WO-2010071837 A1 | 6/2010 |
| WO | WO-2011026911 A1 | 3/2011 |
| WO | WO-2011059610 A1 | 5/2011 |
| WO | WO-2011081205 A1 | 7/2011 |
| WO | WO-2011139107 A2 | 11/2011 |
| WO | WO-2012034363 A1 | 3/2012 |
| WO | WO-2012109075 A1 | 8/2012 |
| WO | WO-2013022766 A1 | 2/2013 |
| WO | WO-2013033167 A1 | 3/2013 |
| WO | WO-2013041652 A1 | 3/2013 |
| WO | WO-2013164769 A1 | 11/2013 |
| WO | WO-2013171640 A1 | 11/2013 |
| WO | WO-2014008214 A1 | 1/2014 |
| WO | WO-2014018725 A1 | 1/2014 |
| WO | WO-2014039375 A1 | 3/2014 |
| WO | WO-2014052699 A1 | 4/2014 |
| WO | WO-2014058691 A1 | 4/2014 |
| WO | 2014151616 A1 | 9/2014 |
| WO | 2015066188 A1 | 5/2015 |

(56) References Cited

FOREIGN PATENT DOCUMENTS

| | | |
|---|---|---|
| WO | 2016/038581 A1 | 3/2016 |
| WO | WO-2016038582 A1 | 3/2016 |
| WO | WO-2016038583 A1 | 3/2016 |
| WO | 2015095819 A2 | 6/2016 |
| WO | 2016115376 A1 | 7/2016 |
| WO | WO-2017037587 A1 | 3/2017 |
| WO | WO-2017212442 A1 * 12/2017 ......... A61K 31/5377 |
| WO | WO-2018051306 A1 | 3/2018 |
| WO | WO-2018107146 A1 | 6/2018 |
| WO | WO-2018203219 A1 | 11/2018 |
| WO | WO-2018213302 A1 | 11/2018 |
| WO | WO-2020046966 A1 | 3/2020 |
| WO | WO-2020128878 A1 | 6/2020 |
| WO | WO-2020230028 A1 | 11/2020 |
| WO | WO-2021165849 A1 | 8/2021 |
| WO | WO-2021229439 A1 | 11/2021 |

OTHER PUBLICATIONS

Nakayama et al. Br J Cancer 99, 2020-2028 (2008). (Year: 2008).*
Sloot et al., "Long-term effects of BRAF inhibitors in melanoma treatment: friend or foe?", Expert Opin. Pharmacother., 15(5), 2014, pp. 589-592.
Alali et al. Chemical interrogation of the neuronal kinome using a primary cellbased screening assay. ACS Chem Biol. 8(5):1027 (2013).
Andreyev et al. Kirsten ras mutations in patients with colorectal cancer: the multicenter "RASCAL" study. J Natl Cancer Inst. 90(9):675 (1998).
Anonymous. History of Changes for Study: NCT02974725 A Phase Ib Study of LXH254-centric Combinations in NSCLC or Melanoma. ClinicalTrials.gov archive Retrieved from the Internet: URL:https://www.clinicaltrials.gov/ct2/history/NCT02974725?V13=View#StudyPageTop [retrieved on Mar. 12, 2020] (Jan. 17, 2019).
Atefi et al. Combination of pan-RAF and MEK inhibitors in NRAS mutant melanoma. Mol Cancer 14(1):27 (2015).
Babchia et al. The P13K/Akt and mTOR/P70S6K signaling pathways in human uveal melanoma cells: interaction with BRaf/ERK. Invest Ophthalmol Vis Sci. 51(1):421 (2010).
Banker Modern Pharmaceutics. Marcel Dekker. New York. (1996) 3 pages.
Belikov. Pharmaceutical Chemistry: Manual. Moscow: MEDpress-inform (pp. 27-29) (2007).
Blasco et al. c-Raf but not B-Raf, is essential for development of K-Ras oncogene-driven non- small cell lung carcinoma. Cancer Cell 19(5):652-63 (2011).
Bos. Ras oncogenes in human cancer: a review. Cancer Res. 49(17):4682 (1989).
Brose et al. BRAF and RAS Mutations in Human Lung Cancer and Melanoma. Cancer Research 62(23):6997-7000 (Dec. 1, 2002).
Cantwell-Dorris et al. BRAFV600E: implications for carcinogenesis and molecular therapy. Mol Cancer Ther. Mar;10(3):385-94 (2011).
CAS Registry No. 730972-83-5, STN Entry Date Aug. 23, 2004.
CAS Registry No. 867157-50-4, STN Entry Date Nov. 10, 2005.
Cox et al. Drugging the undruggable RAS: Mission possible? Nat Rev Drug Discov 13:828-851 (2014).
Dagogo-Jack et al. Impact of BRAF Mutation Class on Disease Characteristics and Clinical Outcomes in BRAF-mutant Lung Cancer. Clin Cancer Res 25(1):158-165 (2019).
Dankner et al., Classifying BRAF alterations in cancer: new rational therapeutic strategies for actionable mutations. Oncogene 37(24):3183-3199 (2018).
Davies et al. Mutations of the BRAF Gene in Human Cancer. Nature 417:949-954 (2002).
De Bono et al. Therapeutics targeting signal transduction for patients with colorectal carcinoma. Br Med Bull. 64:227-254 (2002).
Deng et al., Knowledge-based design of target-focused libraries using protein-ligand interaction constraints. J Med Chem. 49(2):490-500 (2006).

Di Magliano et al. Roles for KRAS in pancreatic tumor development and progression. Gastroenterology 144(6):1220-29 (2013).
Dummer et al., Binimetinib versus dacarbazine in patients with advanced NRAS-mutant melanoma (NEMO): a multicentre, open-label, randomised, phase 3 trial. Lancet Oncol 18:435-445 (2017).
Eisenhauer et al. New response evaluation criteria in solid tumours: revised RECIST guideline (version 1.1). Euro J Cancer 45:228-247 (2009).
Fedorenko et al. Beyond BRAF: where next for melanoma therapy? British I Cancer 112:217-26 (2015).
Gao et al., Integrative analysis of complex cancer genomics and clinical profiles using the cBioPortal. Science signaling 6(269):pi1 (2013).
Golub et al., Molecular classification of cancer: class discovery and class prediction by gene expression monitoring. Science. 286(5439):531-537 (1999).
Gopalsamy et al. Hit to lead optimization of pyrazolo[15a]pyrimidines as BRaf kinase inhibitors. Bioorg Med Chem Lett. 19(24):6890 (2009).
Gura. Cancer Models: Systems for identifying new drugs are often faulty. Science 278(5340):1041-42 (Nov. 1997).
Hatzivassiliou et al. RAF inhibitors prime wildtype RAF to activate the MAPK pathway and enhance growth. Nature. 464:4315 (2010) (Includes Methods page and Supplementary Information).
Heidorn et al. Kinase-Dead BRAF and Oncogenic RAS Cooperate to Drive Tumor Progression through CRAF. Cell 140(2):209-221 (2010).
Hoshino et al. Constitutive activation of the 41-/43-kDa mitogen-activated protein kinase signaling pathway in human tumors. Oncogene 18(3):813-22 (1999).
Jakob et al. NRAS mutation status is an independent prognostic factor in metastatic melanoma. Cancer 118(16):4014-4023 (2012).
Jensen. A note on the term "Chalcogen." J Chem Edu 74(9):1063-4 (1997).
Johnson et al. Relationships Between Drug Activity in NCI Preclinical in Vitro and in Vivo Models and Early Clinical Trials. Br J Cancer 84(10):1424-1431 (2001).
Kawasaki et al. The second messenger phosphatidylinositol5phosphate facilitates antiviral innate immune signaling. Cell Host & Microbe. 14(2):148-58 (2013).
Kharkevich D.A. Pharmacology. Textbook, 2010, 10th edition, pp. 72-82.
Khimicheskiy Entsiklopedicheskiy Slovar. Chemical Encyclopedic Dictionary, Moscow: Sovetskaya Entsiklopediya, 1983, pp. 130-131.
Kim et al., Synthesis and biological evaluation of 4(5)-(6-alkylpyridin-2-yl)imidazoles as transforming growth factor-beta type 1 receptor kinase inhibitors. Journal of Medicinal Chemistry 50:3143-3147 (2007).
Kim et al., Synthesis of heteroaryl substituted imidazole derivatives. Bull Korean Chem Soc. 21(3):345-7 (2000).
Knickelbein et al. Mutant KRAS as a critical determinant of the therapeutic response of colorectal cancer. Genes & Disease 2(1):4-12 (2015).
Krayushkin et al., Photochromic dihetarylethenes. 7. Synthesis of bis(thienylazoles), photochromic analogs of diarylethenes. Russian Chemical Bulletin. International Edition 50(1):116-21 (2001).
Lala et al. Role of nitric oxide in tumor progression: Lessons from experimental tumors. Cancer and Metastasis Reviews 17(1):91-106 (1998).
Lamba et al., RAF suppression synergizes with MEK inhibition in KRAS mutant cancer cells. Cell Rep 8(5):1475-83 (2014).
Lambert et al. Targeting the P13K and MAPK pathways to treat Kaposi's-sarcoma-associated herpes virus infection and pathogenesis. Expert Opin Ther Targets 11(5):589-99 (2007).
Lito et al. Disruption of CRAF Mediated MEK Activation Is Required for Effective MEK Inhibition in KRAS Mutant Tumors. Cancer Cell 25:697-710 (2014).
Martin et al. Inhibition of PIKfyve by YM201636 dysregulates autophagy and leads to apoptosis-independent neuronal cell death. PLoS One 8(3):114 (2013).
Moore et al. Abstract 1816: Phase I study of the raf1 kinase inhibitor BAY 439006 in patients with advanced refractory solid tumors.

(56) References Cited

OTHER PUBLICATIONS

Proceedings of the American Society of Clinical Oncology. (2002) . . . http://www.asco.org/portal/site/ASCO/template.RAW/menuitem.34d60f5624ba07fd506fe . . . Last accessed Dec. 3, 2008. 2 pages.
Nakayama et al. KRAS or BRAF mutation status is a useful predictor of sensitivity to MEK inhibition in ovarian cancer. British J. Cancer 99 (12):2020-28 (2008).
Negrao et al. Molecular Landscape of BRAF-Mutant NSCLC Reveals an Association Between Clonality and Driver Mutations and Identifies Targetable Non-V600 Driver Mutations. J Thorac Oncol 15(10):1611-1623 (Jun. 13, 2020).
Paik et al. Clinical characteristics of patients with lung adenocarcinomas harboring BRAF mutations. J Clin Oncol. 29(15):2046-51 (2011).
Pao et al. KRAS mutations and primary resistance of lung adenocarcinomas to gefitinib or erlotinib. PLoS Med. 2(1):e17 (Jan. 2005).
Patani et al. Bioisosterism: A Rational Approach in Drug Design. Chem. Rev. 96:3147-3176 (1996).
PCT/IB2017/055641 International Invitation to Pay Additional Fees dated Nov. 29, 2017.
PCT/IB2017/055641 International Search Report and Written Opinion dated Feb. 2, 2018.
PCT/IB2018/052989 International Search Report and Written Opinion dated Jul. 24, 2018.
PCT/IB2020/054491 International Search Report and Written Opinion dated Jul. 7, 2020.
PCT/IB2021/051336 International Search Report and Written Opinion dated May 27, 2021.
PCT/IB2021/054013 International Search Report and Written Opinion dated Oct. 19, 2021.
PCT/US2014/026107 International Search Report and Written Opinion dated May 27, 2014.
Pearce et al. Chapter 18: Failure modes in anticancer drug discovery and development, Cancer Drug Design and Discovery Edited by Stephen Neidle pp. 424-435 (2008).
Pollock et al. High frequency of BRAF mutations in nevi. Nat Genet. 33(1):1920 (2003).
Poulikakos et al. RAF inhibitors transactivate RAF dimers and ERK signaling in cells with wild-type BRAF. Nature 464(7287):427-430 (2010).
Ramurthy et al. Design and Discovery of N-(3-(2-(2-Hydroxyethoxy)-6-morpholinopyridin-4-yl)-4-methylphenyl)-2-(trifluoromethyl)isonicotinamide, a Selective, Efficacious, and Well-Tolerated RAF Inhibitor Targeting RAS Mutant Cancers: The Path to the Clinic. J Med Chem 63(5):2013-2027 (2020).
Revesz et al., SAR of 2,6-diamino-3,5-difluoropyridinyl substituted heterocycles as novel p38MAP kinase inhibitors. Bioorg Med Chem Lett. 12(16):2109-12 (2002).
Rowinsky et al. Ras protein farnesyltransferase: A strategic target for anticancer therapeutic development. J Clin Oncol. 17(11):3631 (1999).
Samylina et al., Biopharmaceutical aspects of pharmacopoeial substances. Farmatsiya 8:29-32 (2012).
Scharovsky et al. Inhibition of ras oncogene: a novel approach to antineoplastic therapy. J Biomed Sci. 7(4):292-8 (2000).
Sholl et al. Institutional implementation of clinical tumor profiling on an unselected cancer population. JCI Insight 1:e87062 (2016).
Simone. Oncology: Introduction, Cecil Textbook of Medicine, 20th Edition, vol. 1004-1010 (1996).
Spring et al. Targeting the cyclin D-cyclin-dependent kinase (CDK)4/6-retinoblastoma pathway with selective CDK 4/6 inhibitors in hormone receptor-positive breast cancer: rational, current status, and future directions HHS Public Access. Discov Med 21(113):65-74 (2016).
Strumberg et al. Abstract 121: Final results of a phase I pharmacokinetic and pharmacodynamic study of the raf kinase inhibitor BAY 439006 in patients with solid tumors. Proceedings of the American Society of Clinical Oncology. (2002). http://www.asco.oreportal/site/ASCO/template.RAW/menuitem.34d60f5624ba07fd506fe . . . Last accessed Dec. 3, 2008. 2 pages.
Therasse et al. New guidelines to evaluate the response to treatment in solid tumors: European Organization for Research and Treatment of Cancer, National Cancer Institute of the United States, National Cancer Institute of Canada. J Natl Cancer Inst 92:205-216 (2000).
Tsai, et al. Discovery of a selective inhibitor of oncogenic B-Raf kinase with potent antimelanoma activity. PNAS. 2008; 105(8):3041-3046.
U.S. Appl. No. 14/204,823 Office Action dated Jan. 8, 2015.
U.S. Appl. No. 14/204,823 Office Action dated Jun. 4, 2015.
U.S. Appl. No. 15/601,423 Office Action dated Apr. 4, 2018.
U.S. Appl. No. 16/274,165 Office Action dated Oct. 2, 2019.
U.S. Appl. No. 16/332,120 Office Action dated Apr. 30, 2020.
U.S. Appl. No. 16/610,482 Office Action dated Jan. 22, 2021.
Weekes et al., Abstract CT107: A Phase Ib study to evaluate the MEK inhibitor cobimetinib in combination with the ERK1/2 inhibitor GDC-0994 in patients with advanced solid tumors. AACR Annual Meeting 2017. Apr. 1-5, 2017.
Wenglowsky et al. Pyrazolopyridine inhibitors of BRafV600E. Part 4: Rational design and kinase selectivity profile of cell potent type II inhibitors. Bioorg Med Chem Lett. 22(19):6237-41 (2012).
White et al., Chemiluminescence in liquid solutions: The chemiluminescence of lophine and its derivatives. Photochemistry and Photobiology 4:1129-55 (1965).
Wolf et al. 1387P: Phase Ib study of LXH254 + LTT462 in patients with KRAS- or BRAF-mutant NSCLC. Annals of Oncology 31(S4):S881-S882 (Sep. 1, 2020).
Wolff. Burger's Medicinal Chemistry and Drug Discovery. 5th Ed. Part 1, pp. 975-977 (1995).
Wolin et al., Dual binding site inhibitors of B-RAF kinase. Bioorg Med Chem Lett 18:2825-9 (2008).
Yuen et al. Similarity of the phenotypic patterns associated with BRAF and KRAS mutations in colorectal neoplasia. Cancer Res. 62(22):6451-6455 (2002).
Zeitouni et al. KRAS Mutant Pancreatic Cancer: No Lone Path to an Effective Treatment. Cancer (Basel) 8(4):45 (Apr. 2016).
Zhang et al., The genomic landscape of cutaneous melanoma. Pigment Cell Melanoma Res 29:266-283 (2016).
Zheng et al., Anchored multiplex PCR for targeted next-generation sequencing. Nat Med 20:1479-84 (2014).
Zuccotto et al. Through the "Gatekeeper Door": Exploring the active kinase conformation. J Med Chem. 53(7):2681-94 (2010).
Whittaker et al., "Combined Pan-RAF and MEK Inhibition Overcomes Multiple Resistance Mechanisms to Selective RAF Inhibitors", Molecular Cancer Therapeutics, 14(12):2700-2711. 2015.

* cited by examiner

THERAPEUTIC COMBINATIONS COMPRISING A C-RAF INHIBITOR

CROSS-REFERENCE TO RELATED APPLICATIONS

This application is a U.S. Continuation of U.S. patent application Ser. No. 16/332,120 filed 11 Mar. 2019, which is a 371 U.S. national phase application of international application number PCT/IB2017/055641, filed 18 Sep. 2017, which application claims the benefit of priority under 35 U.S.C. § 119(e) to U.S. Provisional Patent Application No. 62/396,504, filed 19 Sep. 2016. The disclosure of these applications are incorporated herein by reference in their entirety and for all purposes.

FIELD OF THE INVENTION

The present invention relates to the use of a RAF inhibitor, particularly an inhibitor of c-RAF (C-RAF or CRAF), for the treatment of a cancer which is an advanced solid tumor that harbors mitogen-activated protein kinase (MAPK) alterations, such as KRAS-mutant tumors, and in particular, KRAS-mutant NSCLC (non-small cell lung cancer), melanoma, pancreatic cancer, colorectal cancer and ovarian cancer. It particularly relates to therapeutic combinations using at least one RAF inhibitor for treatment of cancers.

The present invention also relates to the use of an ERK inhibitor (ERKi) for treatment of a cancer, especially a cancer having a KRAS-mutation and in particular a gain-of-function mutation of KRAS, including lung cancer (especially NSCLC), melanoma, pancreatic cancer, and ovarian cancer.

The invention further relates to a pharmaceutical combination which comprises (a) at least one ERK inhibitor (ERKi), and (b) a Raf inhibitor that is preferably a c-RAF (CRAF) inhibitor that may also inhibit b-Raf, where the two compounds are prepared and/or used for simultaneous, separate or sequential administration for the treatment of a proliferative disease, and to a pharmaceutical composition comprising such combination; a method of treating a subject having a proliferative disease comprising administration of said combination to a subject in need thereof; use of such combination for the treatment of proliferative disease; and a commercial package comprising such combination. In the invention, said proliferative disease is often a solid tumor that harbors Mitogen-activated protein kinase (MAPK) alterations, such as KRAS-mutant tumors and in particular KRAS-mutant NSCLC (non-small cell lung cancer), melanoma, pancreatic cancer, colorectal cancer and ovarian cancer. Typically, the CRAF inhibitor and the ERK inhibitor are both low-molecular weight compounds and in particular the invention relates to combinations of Compound A and Compound B for use as described herein.

In particular, there is provided a pharmaceutical combination comprising Compound A, or a pharmaceutically acceptable salt thereof, and Compound B, or a pharmaceutically acceptable salt thereof. This pharmaceutical combination may be particularly useful in the treatment of KRAS or BRAF mutant NSCLC, including advanced or metastatic KRAS or BRAF mutant NSCLC.

BACKGROUND

The RAS/RAF/MEK/ERK or MAPK pathway is a key signaling cascade that drives cell proliferation, differentiation, and survival. Dysregulation of this pathway underlies many instances of tumorigenesis. Aberrant signaling or inappropriate activation of the MAPK pathway has been shown in multiple tumor types, including melanoma, lung and pancreatic cancer, and can occur through several distinct mechanisms, including activating mutations in RAS and BRAF. RAS is a superfamily of GTPases, and includes KRAS (v-Ki-ras2 Kirsten rat sarcoma viral oncogene homolog), which is a regulated signaling protein that can be turned on (activated) by various single-point mutations, which are known as gain of function mutations. The MAPK pathway is frequently mutated in human cancer with KRAS and BRAF mutations being among the most frequent (approximately 30%). RAS mutations, particularly gain of function mutations, have been detected in 9-30% of all cancers, with KRAS mutations having the highest prevalence (86%), followed by NRAS (11%), and, infrequently, HRAS (3%) (Cox A D, Fesik S W, Kimmelman A C, et al (2014), Nat Rev Drug Discov. November; 13(11):828-51.). Although selective BRAF inhibitors (BRAFi), and to a lesser extent, MEK inhibitors (MEKi) have demonstrated good activity in BRAF-mutant tumors, currently no effective therapies exist for KRAS-mutant tumors (Cantwell-Dorris E R, O'Leary J J, Sheils O M (2011) *Mol Cancer Ther*. March; 10(3):385-94.).

Emerging evidence on the role of CRAF in mediating KRAS signaling and in the development of KRAS-mutant non-small cell lung cancer (NSCLC) makes it a suitable target for therapeutic intervention (Blasco R B, Francoz S, Santamaria D, et al (2011) *c-Raf but not B-Raf is essential for development of K-Ras oncogene-driven non-small cell lung carcinoma*. Cancer Cell. 2011 May 17; 19(5):652-63.). CRAF was shown to promote feedback-mediated pathway reactivation following MEKi treatment in KRAS-mutant cancers (Lito P, Saborowski A, Yue J, et al (2014) *Disruption of CRAF Mediated MEK Activation Is Required for Effective MEK Inhibition in KRAS Mutant Tumors*. Cancer Cell 25, 697-710, Lamba et al 2014). In addition, CRAF plays an essential role in mediating paradoxical activation following BRAFi treatment (Poulikakos P I, Zhang C, Bollag G, et al. (2010), Nature. March 18; 464(7287):427-30, Hatzivassiliou et al 2010, Heidorn et al 2010). Thus, selective pan-RAF inhibitors that potently inhibit the activity of CRAF and BRAF could be effective in blocking BRAF-mutant tumors and RAS-mutant driven tumorigenesis and may also alleviate feedback activation. Compound A described herein is a potent inhibitor of both CRAF and BRAF.

Lung cancer is a common type of cancer that affects men and women around the globe. NSCLC is the most common type (roughly 85%) of lung cancer with approximately 70% of these patients presenting with advanced disease (Stage IIIB or Stage IV) at the time of diagnosis. About 30% of NSCLC tumors contain activating KRAS mutations, and these mutations are associated with resistance to EGFR tyrosine kinase inhibitors (TKIs) (Pao W, Wang T Y, Riely G J, et al (2005) PLoS Med; 2(1): e17). Activating KRAS mutations are also found in melanoma (*British J. Cancer* 112, 217-26 (2015)), pancreatic cancer (Gastroenterology vol. 144(6), 1220-29 (2013)) and ovarian cancer (*British J. Cancer* 99 (12), 2020-28 (2008)). BRAF mutations have been observed in up to 3% of NSCLC and have also been described as a resistance mechanism in EGFR mutation positive NSCLC.

Direct inhibition of KRAS has proved challenging. To date, no approved targeted therapies are available for patients with KRAS-mutant cancers such as NSCLC. There is thus a high unmet medical need for patients suffering from KRAS mutant NSCLC and for patients suffering from BRAF mutant NSCLC. There is a need for targeted therapy that is safe and/or well tolerated. A therapy which results in durable and sustained responses in a clinical setting would also be beneficial.

SUMMARY

The present invention also provides a pharmaceutical combination which comprises (a) a CRAF inhibitor which is Compound A,

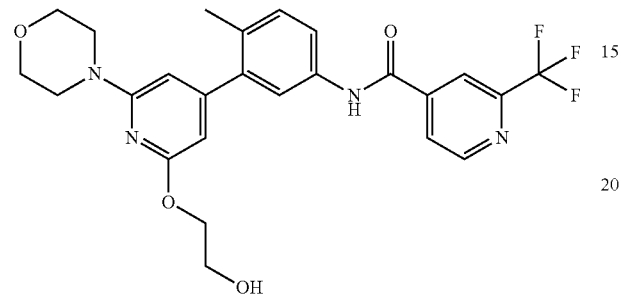

or a pharmaceutically acceptable salt thereof, and
(b) an ERK inhibitor which is Compound B,

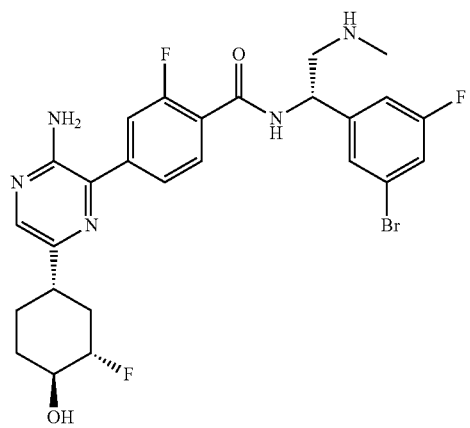 [SMILES: CNC[C@@H](NC(=O)c1ccc(-c2nc([C@H]3CC[C@H](O)[C@@H](F)C3)cnc2N)cc1F)c1cc(F)cc(Br)c1]

or a pharmaceutically acceptable salt thereof. This combination is referred herein as the "combination of the invention".

The present invention further provides a pharmaceutical combination comprising a c-Raf kinase inhibitor, which is Compound A, or a pharmaceutically acceptable salt thereof, and an ERK inhibitor, which is Compound B, or a pharmaceutically acceptable salt thereof, as described herein, for simultaneous, separate or sequential (in any order) administration, for use in the treatment of a proliferative disease. The present invention is particularly related to the combination of the invention for use in the treatment of a proliferative disease characterized by activating mutations in the MAPK pathway, and in particular by one or more mutations in KRAS or BRAF. The present invention is particularly related to the treatment of KRAS-mutant NSCLC (non-small cell lung cancer), BRAF-mutant NSCLC, KRAS-mutant pancreatic cancer, KRAS-mutant colorectal cancer (CRC) and KRAS-mutant ovarian cancer.

Compound A is an adenosine triphosphate (ATP)-competitive inhibitor of BRAF (also referred to herein as b-RAF or b-Raf) and CRAF (also referred to herein as c-RAF or c-Raf) protein kinases. Throughout the present disclosure, Compound A is also referred to as a c-RAF (or CRAF) inhibitor or a C-RAF/c-Raf kinase inhibitor.

Compound A is N-(3-(2-(2-hydroxyethoxy)-6-morpholinopyridin-4-yl)-4-methylphenyl)-2-(trifluoromethyl) isonicotinamide and is the compound of the following structure:

Compound A

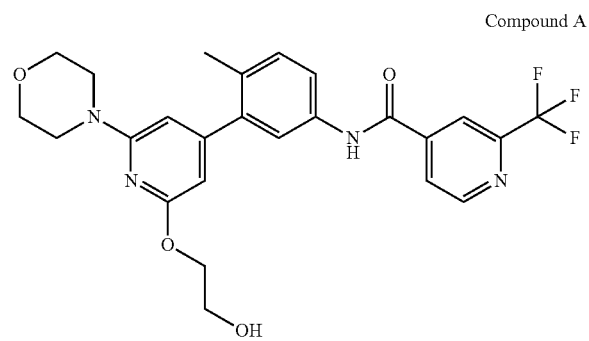 [SMILES: Cc1ccc(NC(=O)c2ccnc(C(F)(F)F)c2)cc1-c1cc(OCCO)nc(N2CCOCC2)c1]

In cell-based assays, Compound A has demonstrated anti-proliferative activity in cell lines that contain a variety of mutations that activate MAPK signaling. In vivo, treatment with Compound A generated tumor regression in several KRAS-mutant models including the NSCLC-derived Calu-6 (KRAS Q61K) and NCI-H358 (KRAS G12C). Collectively, the in vitro and in vivo MAPK-pathway suppression and anti-proliferative activity observed for Compound A at well-tolerated doses suggests that Compound A may have anti-tumor activity in patients with tumors harboring activating lesions in the MAPK pathway. Moreover, Compound A is a Type 2 ATP-competitive inhibitor of both B-Raf and C-Raf that keeps the kinase pocket in an inactive conformation, thereby reducing the paradoxical activation seen with many B-Raf inhibitors, and blocking mutant RAS-driven signaling and cell proliferation. Compound A has exhibited efficacy in numerous MAPK-driven human cancer cell lines and in xenograft tumors representing model tumors harboring human lesions in KRAS, NRAS and BRAF oncogenes.

Compound B is an inhibitor of extracellular signal-regulated kinases 1 and 2 (ERK 1/2). Compound B is known by the name of 4-(3-amino-6-((1S,3S,4S)-3-fluoro-4-hydroxycyclohexyl)pyrazin-2-yl)-N-((S)-1-(3-bromo-5-fluorophenyl)-2-(methylamino)ethyl)-2-fluorobenzamide and is the compound of the following structure.

Compound B

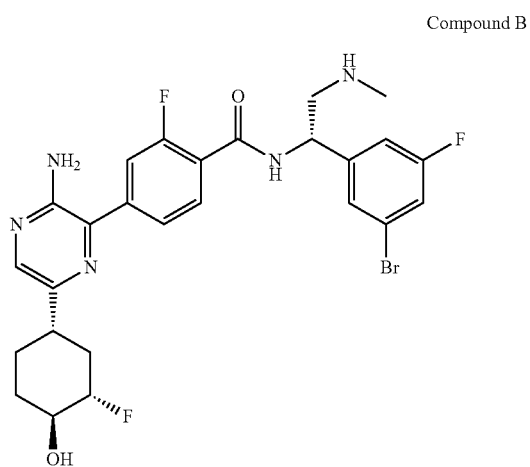

Compound B has been shown to be active as a single-agent therapy in models of various solid tumors, and was especially effective when used in combination with a second anticancer therapeutic agent. For example, in models of pancreatic ductal adenocarcinoma (PDAC), an especially difficult cancer to treat (5-year survival rate for PDAC is 7% according to Cancers (Basel), vol. 8(4), 45 (April 2016)), Compound B in combination with several different anticancer agents exhibited significant tumor shrinkage and was more efficacious than expected based on the single-agent activity of the components of certain combinations. In particular, combinations of Compound B with Compound A demonstrated increased depth and durability of tumor response compared to either single-agent therapy in a human NSCLC xenograft model, Calu-6.

Thus, it is expected that vertical MAPK (mitogen activated protein kinase) inhibition combining a pan-RAF inhibitor such as Compound A with an ERK1/2 kinase inhibitor such as Compound B will optimize suppression of MAPK signaling in KRAS and BRAF mutant NSCLC. This combination may also help to prevent the emergence of resistance to the combination of BRAF and MEK (mitogen-activated protein kinase kinase) inhibitors in BRAFV600E-mutant NSCLC.

Accordingly, the invention provides compositions and methods using Compound B in combination with a RAF inhibitor, and in particular with Compound A, for treating solid tumors, particularly tumors that express KRAS mutations, including NSCLC and especially KRAS-mutant NSCLC, and also BRAF mutant NSCL, including BRAFV600E-mutant NSCLC.

Disclosed herein are pharmaceutical combinations which comprise (a) a c-RAF inhibitor, such as Compound A, or a pharmaceutically acceptable salt thereof, and (b) an ERK inhibitor such as Compound B, or a pharmaceutically acceptable salt thereof, for simultaneous, separate or sequential administration for the treatment of a proliferative disease, particularly a solid tumor that harbors Mitogen-activated protein kinase (MAPK) alterations, such as a KRAS-mutant tumors, and certain BRAF-mutant tumors. These include KRAS-mutant NSCLC (non-small cell lung cancer), BRAF-mutant NSCLC (non-small cell lung cancer), KRAS-mutant and BRAF-mutant NSCLC (non-small cell lung cancer), KRAS-mutant pancreatic cancer, KRAS-mutant colorectal cancer (CRC) and KRAS-mutant ovarian cancer. The present invention also provides the pharmaceutical combination of the invention for use in the treatment of BRAF V600-mutant melanoma including relapsed or refractory BRAF V600-mutant melanoma. Also disclosed are a pharmaceutical composition comprising such combination; a method of treating a subject having a proliferative disease comprising administration of such combination to a subject in need thereof use of such combination for the treatment of proliferative disease; and a commercial package comprising such combination. Other features, objects, and advantages of the invention will be apparent from the description and drawings, and from the claims.

DETAILED DESCRIPTION

Figure 1A:
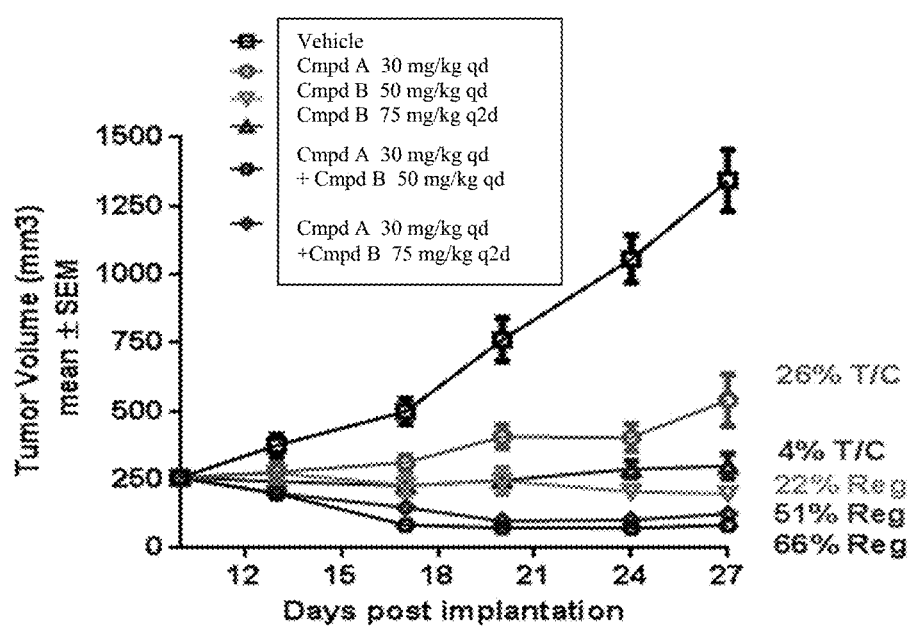
FIG. 1A—depicts anti-tumor efficacy of Compound A and Compound B separately and used together in Calu-6 human NSCLC subcutaneous xenograft tumor models in mice. Compounds were administered orally either daily (qd) or every other day (q2d) as indicated.

The pharmaceutical combination of the invention is a pharmaceutical combination of Compound A, or a pharmaceutically acceptable salt thereof, and Compound B, or a pharmaceutically acceptable salt thereof. In a preferred embodiment, there is provided the pharmaceutical combination of the invention for use in treating a proliferative disease selected from KRAS-mutant NSCLC (non-small cell lung cancer), BRAF-mutant NSCLC (including BRAF BRAFV600E-mutant NSCLC), KRAS-mutant pancreatic cancer, KRAS-mutant colorectal cancer (CRC) and KRAS-mutant ovarian cancer. Patients likely to benefit from the pharmaceutical combination include patients with advanced or metastatic disease, e.g. NSCLC patients, with a diagnosis of advanced or metastatic KRAS or BRAF mutant NSCLC, who may have progressed after receiving standard of care.

CRAF Kinase Inhibitor

The CRAF kinase inhibitors of the present invention include Compound A. Compound A is disclosed as example 1156 in WO2014/151616. WO2014/151616 also describes its preparation and pharmaceutical compositions comprising Compound A.

In a preferred embodiment of the methods, treatments, combination and compositions described herein, the CRAF inhibitor is Compound A, or a pharmaceutically acceptable salt thereof.

Compound A has the following structure:

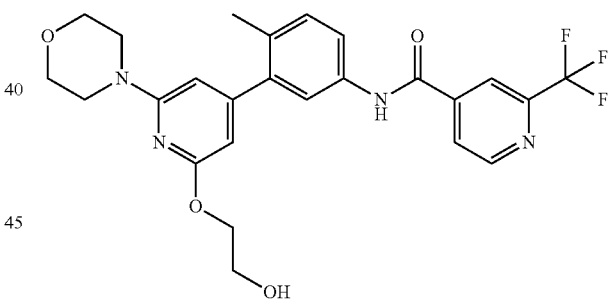

Compound A (Compound A) is also known by the name of N-(3-(2-(2-hydroxyethoxy)-6-morpholinopyridin-4-yl)-4-methylphenyl)-2-(trifluoromethyl)isonicotinamide.

In cell-based assays, Compound A has demonstrated anti-proliferative activity in cell lines that contain a variety of mutations that activate MAPK signaling. In vivo, treatment with Compound A generated tumor regression in several KRAS-mutant models including the NSCLC-derived Calu-6 (KRAS Q61K) and NCI-H358 (KRAS G12C). Collectively, the in vitro and in vivo MAPK-pathway suppression and anti-proliferative activity observed for Compound A at well-tolerated doses suggests that Compound A may have anti-tumor activity in patients with tumors harboring activating lesions in the MAPK pathway. Moreover, Compound A is a Type 2 ATP-competitive inhibitor of both B-Raf and C-Raf that keeps the kinase pocket in an inactive conformation, thereby reducing the paradoxical activation seen with many B-Raf inhibitors, and blocking mutant RAS-driven signaling and cell proliferation. Compound A has exhibited efficacy in numerous MAPK-driven human cancer cell lines and in xenograft tumors representing model tumors harboring human lesions in KRAS, NRAS and BRAF oncogenes.

Based on the mechanism of action of Compound A, preclinical data and published literature on the importance of CRAF in MAPK pathway regulation, Compound A, in combination with at least one other inhibitor of the MAPK pathway such as Compound B, can be useful in the treatment of patients with advanced solid tumors harboring MAPK pathway alterations. Compound A may be used to treat (e.g., one or more of reducing, inhibiting, or delaying progression) a proliferative disease which is an advanced solid tumor that harbors Mitogen-activated protein kinase (MAPK) alterations, such as KRAS-mutant tumors, and in particular, tumors expressing at least one gain of function mutation of RAS or RAF, including lung cancer, NSCLC (non-small cell lung cancer), ovarian cancer, pancreatic cancer, colorectal cancer or melanoma, in a subject in need of such treatment.

ERK Inhibitors

The ERKi compound used for the invention herein is typically Compound B, either in free form or as a pharmaceutically acceptable salt.

Compound B is an inhibitor of extracellular signal-regulated kinases 1 and 2 (ERK 1/2). This compound is disclosed and its preparation and pharmaceutical compositions comprising this compound are described in published PCT patent application WO 2015/066188. Compound B has the following structure:

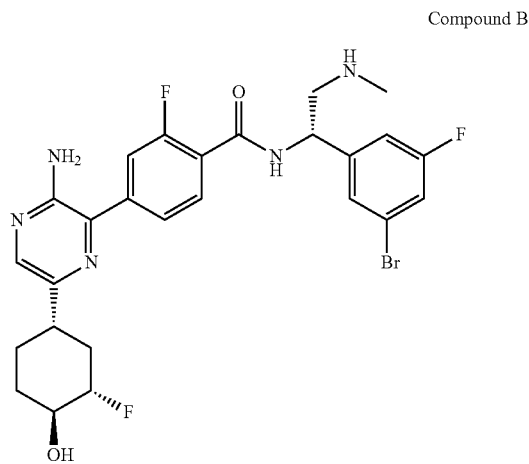 [SMILES: CNC[C@@H](NC(=O)c1ccc(-c2nc([C@H]3CC[C@H](O)[C@@H](F)C3)cnc2N)cc1F)c1cc(F)cc(Br)c1]

Compound B

In some embodiments, the hydrochloride salt of Compound B is used.

Therapeutic Uses

In one embodiment, the invention features a method of treating (e.g., inhibiting, reducing, ameliorating, or preventing) a disorder, e.g., a hyperproliferative condition or disorder (e.g., a cancer) in a subject. The method includes administering to a subject, in combination with a c-RAF inhibitor, an ERK inhibitor; in certain embodiments, the c-RAF inhibitor is Compound A, and the ERK inhibitor is Compound B. Suitable dosages and administration schedules for using these compounds in such methods are described herein.

In some embodiments, the proliferative disorder is a KRAS-mutant tumor such as a tumor expressing at least one gain of function KRAS mutation as described herein, and in particular, KRAS-mutant cancers such as NSCLC (non-small cell lung cancer). Included are tumors having BRAF mutations, including V600E and others, e.g., NSCLC having at least one V600E or other BRAF mutation, whether typical or atypical. The CRAF inhibitor for use in the methods, treatments and combinations disclosed herein is a potent inhibitor of at least CRAF, and optionally also of BRAF. In some embodiments, the CRAF inhibitor, or a pharmaceutically acceptable salt thereof, is administered orally. In some embodiments, the CRAF inhibitor is Compound A or a pharmaceutically acceptable salt thereof.

When describing a dosage herein as 'about' a specified amount, the actual dosage can vary by up to 10%, e.g. 5%, from the stated amount: this usage of 'about' recognizes that the precise amount in a given dosage form may differ slightly from an intended amount for various reasons without materially affecting the in vivo effect of the administered compound. The skilled person will understand that where a dose or dosage of a therapeutic compound is quoted herein, that amount refers to the amount of the therapeutic compound in its free form.

The unit dosage of the CRAF inhibitor may be administered once daily, or twice daily, or three times daily, or four times daily, with the actual dosage and timing of administration determined by criteria such as the patient's age, weight, and gender; the extent and severity of the cancer to be treated; and the judgment of a treating physician.

In one embodiment, Compound A is prepared for oral administration and is administered orally at a dose of 100 mg, 150 mg, 200 mg, 250 mg, 300 mg, or 400 mg delivered up to four times daily: a dose of 100 mg once or twice daily is projected to provide a plasma concentration in human subjects that could be efficacious in humans based on allometric scaling of corresponding plasma levels in animals, and a dose of 200 mg up to four times daily may be administered to achieve greater efficacy while still providing a satisfactory therapeutic index. In some embodiments, Compound A is administered once daily at a dose of 100 mg, 200 mg, 250 mg, 300 mg, or 400 mg. Allometric scaling of preclinical models indicates that a daily dose of 300 mg or higher of Compound A, which may be administered once daily or in two, three or four separate doses over the course of a day, as a single agent should provide a therapeutic effect in many indications including solid tumors that contain or express KRAS mutations.

In the combinations of the invention, the therapeutic dosage of Compound A in these subjects is expected to be lower, thus the combination treatments typically use 100 mg, 200 mg, 250 mg, or 300 mg daily dosage of Compound A for such subjects. Suitably, in the combinations and methods of the invention, a dosage of 100 mg, or 200 mg, or 250 mg, or 300 mg of Compound A is administered once daily.

In one embodiment, Compound B is prepared for administration via oral delivery, and may be used as its hydrochloride salt. In some embodiments, the compound or its HCl salt is simply encapsulated in a pharmaceutically acceptable container such as a hard or soft gelcap for oral administration. The gelcaps can be produced in a variety of dosages for flexible administration; for example, gelcaps can be prepared containing about 5 mg, about 20 mg, about 50 mg, or about 100 mg of Compound B or its HCl salt.

In the combinations of the invention and in the therapeutic uses described herein, Compound A, or a pharmaceutically acceptable salt thereof, may be administered at a daily dose of about 100 mg, or about 150 mg, or about 200 mg, or about 250 mg in combination with Compound B, or a pharmaceutically acceptable salt thereof, which may be administered at a daily dose of about 50 mg, or about 75 mg, or about 100 mg or about 150 mg or about 200 mg. For example, Compound A, or a pharmaceutically acceptable salt thereof, may be administered a total dose of about 100 mg Compound A daily and a total dose of about 100 mg Compound B, or a pharmaceutically acceptable salt thereof, daily, the doses being preferably administered once a day. Patients in need thereof may also receive a total dose of about 200 mg Compound A, or a pharmaceutically acceptable salt thereof, daily and a total dose of about 100 mg Compound B, or a pharmaceutically acceptable salt thereof daily, the doses being preferably administered once a day.

Compound A and Compound B can be used together according to methods disclosed herein. The two Compounds can be administered together or separately in any order, depending on the intended dosage amount and frequency of administration, since it is contemplated that the treatments of the invention may be continued for 2 days, 3 days, 4 days, 5 days, 6 days, 1 week, 2 weeks, 3 weeks, 4 weeks, or more than 4 weeks as deemed appropriate to the treating physician, and further as guided using methods described herein to determine a suitable dosage and administration frequency. In the methods and uses disclosed herein, Compound A and/or Compound B may be administered daily for at least five consecutive days.

In another aspect, the invention features a method of reducing an activity (e.g., growth, survival, or viability, or all), of a hyperproliferative (e.g., a cancer) cell. In another aspect, the invention provides methods and compositions using Compound B to treat solid tumors is administered, or prepared for administration, separately, simultaneously, or sequentially with a CRAF inhibitor. It also provides a CRAF inhibitor for use in treating a solid tumor expressing a gain of function mutation in the MAPK pathway such as KRAS-mutant NSCLC (non-small cell lung cancer), BRAF-mutant NSCLC (non-small cell lung cancer), KRAS-mutant and BRAF-mutant NSCLC (non-small cell lung cancer), KRAS-mutant pancreatic cancer, KRAS-mutant colorectal cancer (CRC) and KRAS-mutant ovarian cancer and BRAF V600-mutant melanoma, wherein the CRAF inhibitor is administered, or prepared for administration, separately, simultaneously, or sequentially with an ERK inhibitor such as Compound B. Typically, Compound B is administered orally, and is administered separately, simultaneously or sequentially with the CRAF inhibitor, which is also often administered orally. Suitable methods, administration routes, dosages, and frequency of administration of Compound A and Compound B for use in these methods and compositions are described herein.

In another aspect, the invention provides an ERK 1/2 inhibitor for use in treating KRAS-mutant NSCLC (non-small cell lung cancer) and for use in treating BRAF mutant NSCLC, wherein the ERK 1/2 inhibitor is administered, or prepared for administration, separately, simultaneously, or sequentially with a CRAF inhibitor. It also provides a CRAF inhibitor for use in treating KRAS-mutant NSCLC (non-small cell lung cancer) and for use in treating BRAF mutant NSCLC, wherein the CRAF inhibitor is administered, or prepared for administration, separately, simultaneously, or sequentially with an ERK 1/2 inhibitor. Typically, the ERK 1/2 inhibitor is administered orally, and may be administered separately or sequentially with the CRAF inhibitor, which is also administered orally. Suitable methods, routes, dosages and frequency of administration of the CRAF inhibitor and the ERK 1/2 inhibitor are described herein. In some embodiments, the CRAF inhibitor is Compound A; in some embodiments, the ERK 1/2 inhibitor is Compound B.

The combinations disclosed herein can be administered together in a single composition or administered separately in two or more different compositions, e.g., compositions or dosage forms as described herein. The pharmaceutical combinations described herein, in particular the pharmaceutical combination of the invention, may be a free combination product, i.e. a combination of two or more active ingredients, e.g. Compound A and Compound B, which is administered simultaneously, separately or sequentially as two or more distinct dosage forms. The administration of the therapeutic agents can be in any order. The first agent and the additional agents (e.g., second, third agents) can be administered via the same administration route or via different administration routes.

In another aspect, the invention features a composition comprising Compound A and Compound B, optionally also containing at least one, and optionally more than one, pharmaceutically acceptable excipient or carrier. Such composition is used to treat a solid tumor, typically a solid tumor expressing a KRAS mutation or RAF mutation, often for treatment of NSCLC, and particularly for treating a patient having NSCLC that exhibits at least one KRAS mutation, especially a gain of function mutation such as those described herein.

Non-Small Cell Lung Cancer (NSCLC)

Lung cancer is a common type of cancer that affects men and women around the globe. Non-small cell carcinoma (NSCLC) is the most common type (roughly 85%) of lung cancer with approximately 70% of these patients presenting with advanced disease (Stage IIIB or Stage IV) at the time of diagnosis. While lung cancer is commonly associated with smoking, non-smokers are also subject to lung cancer, particularly NSCLC: diagnosis in non-smokers is often delayed because the association with smoking is high, but 10-15% of lung cancer patients never smoked. About 30% of NSCLC contain activating KRAS mutations, and these mutations are associated with resistance to EGFR TKIs (Pao W, Wang T Y, Riely G J, et al (2005) *PLoS Med;* 2(1): e17).

Immunotherapies currently in development have started to offer significant benefit to lung cancer patients, including those for whom conventional treatments are ineffective. Recently, pembrolizumab (Keytruda®) and nivolumab (Opdivo®), two inhibitors of the PD-1/PD-L1 interaction have been approved for use in NSCLC. However, results indicate that many patients treated with single agent PD-1 inhibitors do not benefit adequately from treatment.

Direct inhibition of KRAS has proved challenging and KRAS-mutant NSCLC remains an elusive target for cancer therapy. To date, no approved targeted therapies are available for patients with KRAS- or BRAF mutant NSCLC.

BRAF mutations have been observed in up to 3% of NSCLC and have also been described as a resistance mechanism in EGFR mutation positive NSCLC (Paik PK, Arcila M E, Fara M, et al (2011). J Clin Oncol. May 20; 29(15):2046-51).

Ovarian Cancer

Ovarian cancer is the most lethal gynecologic cancer and is a heterogeneous disease comprised of a collection of different histologic and molecular subtypes with variable prognosis. The epithelial subtype comprises 90% of ovarian cancers.

The most common histologic subtype of epithelial ovarian cancer is serous carcinoma accounting for 60 to 70% of epithelial ovarian cancers. A two tiered grading system separates serous carcinoma into low-grade serous (LGS) and high-grade serous (HGS) that have different molecular characteristics, immunohistochemical profile, epidemiologic features, and clinical behavior. LGS carcinoma accounts for up to 10% of the serous epithelial ovarian cancers and ovarian carcinomas with KRAS (up to 40%) or BRAF mutations (2-6%) are predominantly LGS carcinomas. LGS carcinoma is chemoresistant, not only to first-line agents, but also in the setting of recurrent disease.

Pancreatic Cancer

The term "pancreatic cancer" as used herein includes pancreatic ductal adenocarcinoma (PDAC). PDAC is the most common type of pancreatic cancer.

KRAS-Mutant Cancer and BRAF-Mutant NSCLC

The present invention provides a pharmaceutical combination comprising (a) a CRAF inhibitor which is Compound A, or a pharmaceutically acceptable salt thereof, and (b) an ERK inhibitor which is Compound B, or a pharmaceutically acceptable salt thereof for use in the treatment of KRAS-mutant NSCLC.

In another aspect the present invention provides a pharmaceutical combination comprising (a) a CRAF inhibitor which is Compound A, or a pharmaceutically acceptable salt thereof, and (b) an ERK inhibitor which is Compound B, or a pharmaceutically acceptable salt thereof for use in the treatment of KRAS-mutant colorectal cancer (CRC).

In another aspect the present invention provides a pharmaceutical combination comprising (a) a CRAF inhibitor which is Compound A, or a pharmaceutically acceptable salt thereof, and (b) an ERK inhibitor which is Compound B, or a pharmaceutically acceptable salt thereof for use in the treatment of KRAS-mutant ovarian cancer.

In another aspect the present invention provides a pharmaceutical combination comprising (a) a CRAF inhibitor which is Compound A, or a pharmaceutically acceptable salt thereof, and (b) an ERK inhibitor which is Compound B, or a pharmaceutically acceptable salt thereof for use in the treatment of KRAS-mutant pancreatic cancer.

In another aspect the present invention provides a pharmaceutical combination comprising (a) a CRAF inhibitor which is Compound A, or a pharmaceutically acceptable salt thereof, and (b) an ERK inhibitor which is Compound B, or a pharmaceutically acceptable salt thereof for use in the treatment of BRAF-mutant NSCLC.

The term "BRAF-mutant" tumor or cancer includes any tumor that exhibits a mutated BRAF protein. Examples of B-Raf mutations include, but are not limited to V600E and V600K. Most of the B-Raf mutations are clustered to two regions: the glycine-rich P loop of the N lobe and the activation segment and flanking regions. V600E mutation has been detected in a variety of cancers, and is due to a substitution of thymine with adenine at nucleotide 1799. This leads to valine (V) being substituted for by glutamate (E) at codon 600 (now referred to as V600E).

The term "KRAS-mutant" tumor or cancer includes any tumor that exhibits a mutated KRAS protein, in particular gain of function KRAS-mutation; especially any G12X, G13X, Q61X or A146XKRAS-mutant, where X is any amino acid other than the one naturally occurring at that position. E.g., a G12V mutation means that a Glycine is substituted with Valine at codon 12. Examples of KRAS mutations in tumors include Q61K, G12V, G12C and A146T. Thus KRAS-mutant NSCLC, CRC, ovarian cancer and pancreatic cancer include, but are not limited to, Q61K, G12V, G12C and A146T NSCLC, Q61K, G12V, G12C and A146T CRC, ovarian cancer or pancreatic cancer. For example, cancers to be treated by the combination therapies disclosed herein include $KRAS^{Q61K}$ lung cancer, $KRAS^{G12D}$ ovarian cancer, $KRAS^{G12D}$ pancreatic cancer and $KRAS^{G12R}$ pancreatic cancer.

The term "BRAF-mutant" tumor or cancer includes any tumor that exhibits a mutated BRAF protein. Examples of B-Raf mutations include, but are not limited to V600E and V600K. Most of the B-Raf mutations are clustered to two regions: the glycine-rich P loop of the N lobe and the activation segment and flanking regions. V600E mutation has been detected in a variety of cancers, and is due to a substitution of thymine with adenine at nucleotide 1799. This leads to valine (V) being substituted for by glutamate (E) at codon 600 (now referred to as V600E).

The cancers treated by the pharmaceutical combinations described herein may be at an early, intermediate or advanced state.

Uses of the Combination Therapies

In one aspect, a method of treating (e.g., one or more of reducing, inhibiting, or delaying progression) proliferative disease which is an advanced solid tumor that harbors one or more Mitogen-activated protein kinase (MAPK) alterations, such as KRAS-mutant tumors, and in particular, KRAS-mutant NSCLC (non-small cell lung cancer) in a subject is provided. The method comprises administering to the subject a combination disclosed herein (e.g., a combination comprising a therapeutically effective amount of ERK 1/2 inhibitor and a therapeutically effective amount of Compound A, or a pharmaceutically acceptable salt thereof).

The combinations as described herein can be administered to the subject systemically (e.g., orally, parenterally, subcutaneously, intravenously, rectally, intramuscularly, intraperitoneally, intranasally, transdermally, or by inhalation or intracavitary installation), topically, or by application to mucous membranes, such as the nose, throat and bronchial tubes. In some embodiments, an ERK 1/2 inhibitor for use in these combinations and methods is administered orally. In some embodiments, a CRAF inhibitor for use in the combinations and methods of the invention is administered orally. Where an ERK 1/2 inhibitor and a CRAF inhibitor are used in combination, both may be administered orally, and may be administered together (at the same time) or separately in any order, following dosing schedules determined by a treating physician; suitable doses and dosing schedules are disclosed herein.

Further Combination Therapies

In certain embodiments, the methods and compositions described herein are administered in combination with one or more other cancer therapy modes such as antibody molecules, chemotherapy, other anti-cancer therapeutic agents (e.g., targeted anti-cancer therapies, gene therapy, viral therapy, RNA therapy bone marrow transplantation, nanotherapy, or oncolytic drugs), cytotoxic agents, immune-based therapies (e.g., cytokines, immunostimulants, or cell-based immune therapies), surgical procedures (e.g., lumpectomy or mastectomy) or radiation procedures, or a combination of any of the foregoing. The additional therapy may be in the form of adjuvant or neoadjuvant therapy. In some embodiments, the additional therapy is an enzymatic inhibitor (e.g., a small molecule enzymatic inhibitor) or a metastatic inhibitor. Exemplary cytotoxic agents that can be administered in combination with the combination of the invention include antimicrotubule agents, topoisomerase inhibitors, anti-metabolites, mitotic inhibitors, alkylating agents, anthracyclines, vinca alkaloids, intercalating agents, agents capable of interfering with a signal transduction pathway, agents that promote apoptosis, proteosome inhibitors, and radiation (e.g., local or whole body irradiation (e.g., gamma irradiation). In other embodiments, the additional therapy is surgery or radiation, or a combination thereof. In other embodiments, the additional therapy is a therapy targeting one or more of PI3K/AKT/mTOR pathway, an HSP90 inhibitor, or a tubulin inhibitor.

Alternatively, or in combination with the aforesaid combinations, the methods and compositions described herein can be administered in combination with one or more of: an immunomodulator (e.g., an activator of a costimulatory molecule or an inhibitor of an inhibitory molecule, e.g., an immune checkpoint molecule); a vaccine, e.g., a therapeutic cancer vaccine; or other forms of cellular immunotherapy.

Any combination and sequence of other therapeutic agents, procedures or modalities (e.g., as described herein) can be used in combination with the treatments of the invention. The compositions and combinations of the invention can be administered before the other treatment methods, concurrently with other treatment methods, between cycles of such other treatments, or during remission of the disorder.

Disclosed herein, are methods, combinations, and compositions comprising an ERK inhibitor and/or a C-Raf inhibitor for use to treat cancers, especially solid tumors expressing at least one gain-of-function mutation in the MAPK pathway.

Selected terms are defined below and throughout the application.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values. In particular, where a dosage is mentioned as 'about' a particular value, it is intended to include a range around the specified value of plus or minus 10%. As is customary in the art, dosages refer to the amount of the therapeutic agent in its free form. For example, when a dosage of 100 mg of Compound B is referred to, and Compound B is used as its hydrochloride salt, the amount of the therapeutic agent used is equivalent to 100 mg of the free form of Compound B.

By "a combination" or "in combination with," it is not intended to imply that the therapy or the therapeutic agents must be physically mixed or administered at the same time and/or formulated for delivery together, although these methods of delivery are within the scope described herein. A therapeutic agent in these combination can be administered concurrently with, prior to, or subsequent to, one or more other additional therapies or therapeutic agents. The therapeutic agents or therapeutic protocol can be administered in any order. In general, each agent will be administered at a dose and/or on a time schedule determined for that agent. It will further be appreciated that the additional therapeutic agent utilized in this combination may be administered together in a single composition or administered separately in different compositions. In general, it is expected that additional therapeutic agents utilized in combination be utilized at levels that do not exceed the levels at which they are utilized individually. In some embodiments, the levels utilized in combination will be lower than those utilized as single-agent therapeutics.

The term "synergistic" as used herein refers to the action of two therapeutic agents such as, for example the c-RAF inhibitor compound of Compound A, and an ERK 1/2 inhibitor compound of Compound B, producing an effect, for example, slowing the symptomatic progression of a proliferative disease, particularly cancer, or symptoms thereof, which is greater that the simple addition of the effects of each drug administered by themselves. A synergistic effect can be calculated, for example, using suitable methods such as those described in (Lehar et al 2009).

In embodiments, the additional therapeutic agent (e.g., the CRAF inhibitor) is administered at a therapeutic or lower-than therapeutic dose relative to a single-agent dose level. In certain embodiments, the concentration of the second therapeutic agent that is required to achieve inhibition, e.g., growth inhibition or tumor shrinkage, is lower when the second therapeutic agent, e.g., the ERK 1/2 inhibitor, is used or administered in combination with the first therapeutic agent than when the second therapeutic agent is administered individually. In certain embodiments, the concentration or dosage of the first therapeutic agent that is required to achieve inhibition, e.g., growth inhibition, is lower when the first therapeutic agent is administered in combination with the second therapeutic agent than when the first therapeutic agent is administered individually. In certain embodiments, in a combination therapy, the concentration or dosage of the second therapeutic agent that is required to achieve inhibition, e.g., growth inhibition, is lower than the therapeutic dose of the second therapeutic agent as a monotherapy, e.g., 10-20%, 20-30%, 30-40%, 40-50%, 50-60%, 60-70%, 70-80%, or 80-90% lower. In certain embodiments, in a combination therapy, the concentration or dosage of the first therapeutic agent that is required to achieve inhibition, e.g., growth inhibition, is lower than the therapeutic dose of the first therapeutic agent as a monotherapy, e.g., 10-20%, 20-30%, 30-40%, 40-50%, 50-60%, 60-70%, 70-80%, or 80-90% lower.

The term "inhibition," "inhibitor," or "antagonist" includes a reduction in a certain parameter, e.g., an activity, of a given molecule or pathway. For example, inhibition of an activity of a targeted kinase (CRAF or ERK 1/2) by 5%, 10%, 20%, 30%, 40% or more is included by this term. Thus, inhibition can be but need not be 100%.

The term "cancer" refers to a disease characterized by the undesired and uncontrolled growth of aberrant cells. Cancer cells can spread locally or through the bloodstream and lymphatic system to other parts of the body. As used herein, the term "cancer" or "tumor" includes premalignant, as well as malignant cancers and tumors.

As used herein, the terms "treat", "treatment" and "treating" refer to the reduction or amelioration of the progression, severity and/or duration of a disorder, e.g., a proliferative disorder, or the amelioration of one or more symptoms (preferably, one or more discernible symptoms) of the disorder resulting from the administration of one or more therapies. In specific embodiments, the terms "treat," "treatment" and "treating" refer to the amelioration of at least one measurable physical parameter of a proliferative disorder, such as growth of a tumor, not necessarily discernible by the patient. In other embodiments the terms "treat", "treatment" and "treating"-refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

Pharmaceutical Compositions and Kits

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation.

Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

The pharmaceutical compositions of the invention may include a "therapeutically effective amount" or a "prophylactically effective amount" of a compound of the invention. A "therapeutically effective amount" refers to an amount effective, at dosages and for periods of time necessary, to achieve the desired therapeutic result. A therapeutically effective amount may vary according to factors such as the disease state, age, sex, and weight of the individual. A therapeutically effective amount is also one in which any toxic or detrimental effects of the CRAF and/or ERK 1/2 inhibitor are outweighed by the therapeutically beneficial effects. A "therapeutically effective dosage" preferably modulates a measurable parameter in a desired manner, e.g., tumor growth rate, by at least about 20%, more preferably by at least about 40%, even more preferably by at least about 60%, and still more preferably by at least about 80% relative to untreated subjects. The ability of a compound to desirably modulate a measurable parameter, e.g., cancer, can be evaluated in an animal model system predictive of efficacy in human tumors to help establish suitable dosing levels and schedules. Alternatively, this property of a composition can be evaluated by examining the ability of the compound to modulate an undesired parameter using in vitro assays known to the skilled practitioner.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Also within the scope of the invention is a kit comprising one or more of the Compounds described herein. The kit can also include one or more other elements: instructions for use; other reagents for use with the compound(s); devices or other materials for preparing the compound for administration, such as a mixing container; pharmaceutically acceptable carriers; and devices or other materials for administration to a subject, such as a syringe.

The combinations of the invention have therapeutic or protective functions or both, and can be used in vivo or ex vivo. For example, these molecules can be administered to cells in culture, in vitro or ex vivo, or to a human subject, to treat, prevent, and/or diagnose a variety of disorders, such as cancers as described herein.

Accordingly, in one aspect, the invention provides a method of enhancing the efficacy of an anticancer compound by using it in combination with another anticancer compound, particularly a method using Compound A together with Compound B to provide enhanced efficacy not safely achievable by administering similar doses of either compound as a single agent. These combinations are particularly useful for treatment of cancers expressing one or more gain of function mutations in the MAPK pathway, particularly mutations in RAS and/or Raf genes.

EXAMPLES

The Examples below are set forth to aid in the understanding of the inventions but are not intended to, and should not be construed to, limit its scope in any way.

Example 1: N-(3-(2-(2-hydroxyethoxy)-6-morpholinopyridin-4-yl)-4-methylphenyl)-2-(trifluoromethyl)isonicotinamide Compound A (Compound A) is a morpholine-substituted biaryl compound of the following structure

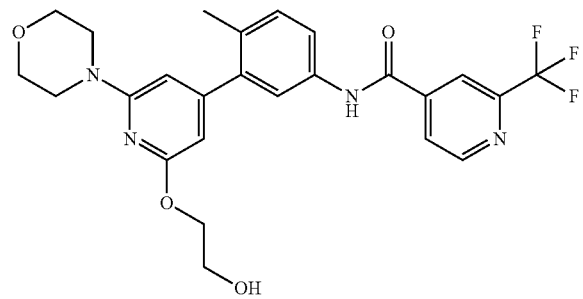 [SMILES: Cc1ccc(NC(=O)c2ccnc(C(F)(F)F)c2)cc1-c1cc(OCCO)nc(N2CCOCC2)c1]

Compound A is Example 1156 in published PCT application WO2014/151616. The preparation of Compound A, pharmaceutically acceptable salts of Compound A and pharmaceutical compositions comprising compound A are also disclosed in the PCT application, e.g see pages 739-741.

Example 1A

In Vitro Raf Activity Determination

The RAF enzymes and the catalytically inactive MEK1 protein substrate were all made in-house using conventional methods. CRAF cDNA was subcloned as full length protein, with Y340E and Y341E activating mutations, into a baculovirus expression vector for Sf9 insect cell expression. h14-3-3 zeta cDNA was subcloned into a baculovirus expression vector for SF9 insect cell expression. Sf9 cells co-expressing both proteins were lysed and subjected to immobilized nickel chromatography and eluted with Imidazole. A second column (StrepII binding column) was used and eluted with desthiobiotin. Protein Tags were removed using Prescission enzyme and the protein was further purified using a flowthrough step to remove tags.

C-Raf FL refers to the full-length C-Raf protein.

Full length MEK1 with an inactivating K97R ATP binding site mutation is utilized as a RAF substrate. The MEK1 cDNA was subcloned with an N-terminal (his)$_6$ tag into a vector for E. Coli expression. The MEK1 substrate was purified from E. Coli lysate by nickel affinity chromatography followed by anion exchange. The final MEK1 preparation was biotinylated (Pierce EZ-Link Sulfo-NHS-LC-Biotin) and concentrated.

Assay Materials

Assay buffer: 50 mM Tris, pH 7.5, 15 mM $MgCl_2$, 0.01% Bovine Serum Albumin (BSA), 1 mM dithiothreitol (DTT)

Stop buffer: 60 mM ethylenediaminetetraacetic acid (EDTA), 0.01% Tween® 20 b-Raf(V600E), active biotinylated Mek, kinase dead

Alpha Screen detection kit (available from PerkinElmer™, #6760617R)

Anti phospho-MEK1/2 (available from Cell Signalling Technology, Inc. #9121)

384 well low volume assay plates (White Greiner® plates)

Assay Conditions b-Raf(V600E) approximately 4 pM c-Raf approximately 4 nM biotinylated Mek, Kinase dead approximately 10 nM ATP 10 uM for BRAF(V600E) and 1 uM for CRAF Pre-incubation time with compounds 60 minutes at room temperature Reaction time 1 or 3 hours at room temperature Assay Protocol Raf and biotinylated Mek, kinase dead, were combined at 2× final concentrations in assay buffer (50 mM Tris, pH 7.5, 15 mM $MgCl_2$, 0.01% BSA and 1 mM DTT) and dispensed 5 ml per well in assay plates (Greiner white 384 well assay plates #781207) containing 0.25 ml of 40× of a Raf kinase inhibitor test compound diluted in 100% DMSO. The plate was incubated for 60 minutes at room temperature.

The Raf kinase activity reaction was started by the addition of 5 mL per well of 2×ATP diluted in assay buffer. After 3 hours (b-Raf(V600E)) or 1 hour (c-Raf). The reactions were stopped and the phosphorylated product was measured using a rabbit anti-p-MEK (Cell Signaling, #9121) antibody and the Alpha Screen IgG (ProteinA) detection Kit (PerkinElmer #6760617R), by the addition of 10 mL to the well of a mixture of the antibody (1:2000 dilution) and detection beads (1:2000 dilution of both beads) in Stop/bead buffer (25 mM EDTA, 50 mM Tris, pH 7.5, 0.01% Tween20). The additions were carried out under dark conditions to protect the detection beads from light. A lid was placed on top of the plate and incubated for 1 hour at room temperature, then the luminescence was read on a PerkinElmer Envision instrument. The concentration of each compound for 50% inhibition ($IC_{50}$) was calculated by non-linear regression using XL Fit data analysis software.

Using the assays described above, compound A exhibited inhibitory efficacy as reported below.

| Compound A is a type II inhibitor of both b-Raf and c-Raf. | | |
| --- | --- | --- |
| Compound | b-Raf IC-50 (µM) | c-Raf FL IC-50 (µM) |
| Compound A | 0.00073 | 0.00020 |

Example 1B

Compound A exhibits activity on numerous human cancer cell lines that express mutations in the MAPK pathway as shown in the following Table. Note that activity is especially strong on cell lines that harbor at least one mutation in BRAF or RAS.

TABLE 1

| Effect of Compound A on proliferation in a panel of human cancer cell lines. | | | | |
| --- | --- | --- | --- | --- |
| Cell Line | $IC_{50}$ [µM] | Tumor Type | BRAF | RAS |
| A375 | 0.24 | Melanoma | V600E | WT |
| WM2664 | 0.45 | Melanoma | V600D | WT |
| IPC298 | 0.25 | Melanoma | WT | NRAS Q61L |

TABLE 1-continued

| Effect of Compound A on proliferation in a panel of human cancer cell lines. | | | | |
| --- | --- | --- | --- | --- |
| Cell Line | $IC_{50}$ [µM] | Tumor Type | BRAF | RAS |
| HeyA8 | 0.21 | Ovarian | G464E | KRAS G12D |
| HCT116 | 0.47 | Colorectal | WT | KRAS G13D |
| Calu-6 | 1.5 | NSCLC | WT | KRAS Q61K |
| HuP-T4 | 0.65 | Pancreas | WT | KRAS G12V |
| PSN1 | 0.68 | Pancreas | WT | KRAS G12R |
| TCC-PAN2 | 0.42 | Pancreas | WT | KRAS G12R |
| NCI-H2073 | 18.2 | NSCLC | WT | WT |
| HCC827 | >20 | NSCLC | WT | WT |
| PC3 | >20 | Prostate | WT | WT |

Different tumor cell lines were treated with dose titrations of Compound A for 72 h, and cell proliferation was determined using the CellTiter-Glo ™ luminescent cell viability assay..

Example 1C

To investigate the activity of Compound A in BRAF V600 mutant melanoma cells refractory to BRAF and/or MEK inhibitors, the anti-proliferative activity of Compound A in the mechanistic models derived from the BRAF V600 melanoma cell line A375 expressing mutations of MEK1/2, NRAS, or a splice variant of BRAF was evaluated. These mutations have been demonstrated in both preclinical studies and clinical samples to confer BRAF and/or MEK inhibitor resistance. Growth inhibitory effects of Compound A in the parental A375 cell line and its derivatives expressing the various mutant alleles, in comparison with efficacy of the BRAF inhibitor Vemurafenib and the MEK inhibitor Selumetinib, are summarized below. The mutations conferred resistance to both the BRAF and MEK inhibitors, leading to greater than 50 fold increases in $IC_{50}$ values. In contrast, the resistant models were still sensitive to Compound A, with only a 2-3 fold increase in $IC_{50}$. These data support the use of Compound A in BRAF V600 melanoma patients who have become refractory to BRAF and/or MEK inhibitors.

| Anti-proliferative effect of Compound A in mechanistic A375 models resistant to BRAF and MEK inhibitors | | | |
| --- | --- | --- | --- |
| Cell Line | Compound A $IC_{50}$ [µM] | Vemurafenib $IC_{50}$ [µM] | Selumetinib $IC_{50}$ [µM] |
| A375 | 0.42 | 0.066 | 0.036 |
| A375/BRAFp61-V600E | 0.72 | 8.51 | >10 |
| A375/MEK1 Q56P | 1.15 | 9.62 | 5.35 |
| A375/MEK1 C121S | 1.14 | 8.7 | 2.33 |
| A375/MEK1 E203K | 1.05 | 5.58 | 1.81 |
| A375/MEK2 Q60P | 1.12 | 5.28 | 4.84 |
| A375/NRAS Q61K | 0.95 | 9.38 | 5.5 |

A375 cell lines were engineered to inducibly express resistance models after treatment with doxycycline. Cells were then treated with serial dilutions of Compound A, Vemurafenib or Selumetinib for 72 hours to assess anti-proliferative activity. Cell proliferation was determined using the CellTiter-Glo ™ luminescent cell viability assay and calculated as percent of DMSO control.

Example 1D

Compound A was formulated with hydroxypropylmethylcellulose/Hypromellose, colloidal silicon dioxide, microcrystalline cellulose, polyvinylpyrrolidone/Povidone and magnesium stearate, and formed into tablets containing about 50 mg of Compound A. A number of tablets sufficient to provide a desired dosage were administered once daily to fasted subjects. Subjects were treated at doses of 100 mg once per day, or 200 mg once per day. Serial blood samples for PK assessments were collected up to 48 hours after the first dose of Compound A (Cycle 1 Day 1), and up to 24 hours after multiple doses (Cycle 1 Day 15). Maximum plasma concentrations (Cmax) of 447 ng/ml and 889 ng/ml were achieved within 4 hours after administration of a single 100 mg dose and single 200 mg dose, respectively. Mean plasma exposure over the dose interval of 24 hours (AUC-tau) on day 1 of dosing was 5679 hr·ng/ml and 10019 hr·ng/ml after the 100 mg and 200 mg doses of Compound A, respectively. The half-life is calculated to be around 23-24 hours in patients. The once daily dosing of 100 mg resulted in slight accumulation of Compound A in plasma, with an accumulation ratio of 1.8. Based on these data, a dosing schedule of once per day was established. As this study is on-going, all data presented are considered preliminary.

Example 2: Anti-Tumor Activity of Compound a in KRAS-Mutant NSCLC Models

H358 Model:
SCID beige female tumor-bearing NCI-H358 mice, n=8 per group, were randomized into 3 groups 14 days post tumor cell inoculation with an average tumor volume range of 259.44-262.47 mm$^3$.

Animals were administered an oral dose of either vehicle, Compound A at 30 mg/kg or 200 mg/kg daily for 14 consecutive days at a dosing volume of 10 ml/kg of animal body weight during course of treatment. Tumor volumes were measured by digital caliper 3 times a week and body weights of all animals were recorded through the course of treatment.

Calu6 Model:
Female nude tumor bearing Calu6 mice, n=6 per group were randomized into treatment groups on day 17 following tumor implantation, when the average tumor volume was 180 mm3. Treatments with compound A were initiated on Day 17 and continued for 16 days. Dosing volume was 10 mL/kg. Tumor volumes were collected at the time of randomization and twice weekly thereafter for the study duration.

Figure 1B:
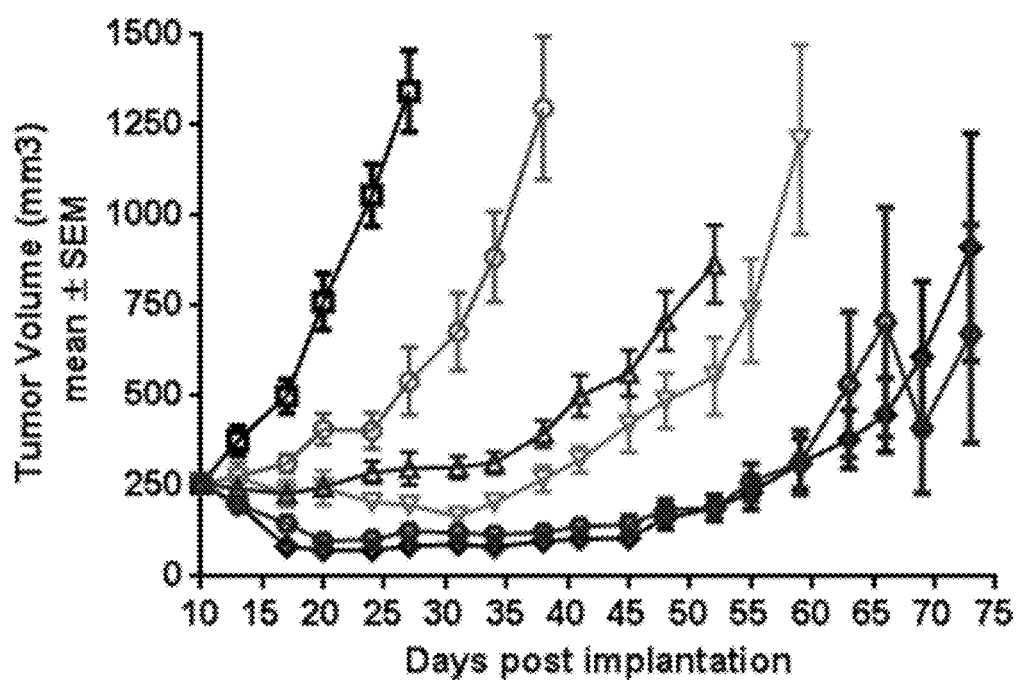
FIG. 1B—depicts durability of response of the treatments shown in FIG. 1A, demonstrating that combination treatments were superior to either single agent treatment.
Figure 1C:
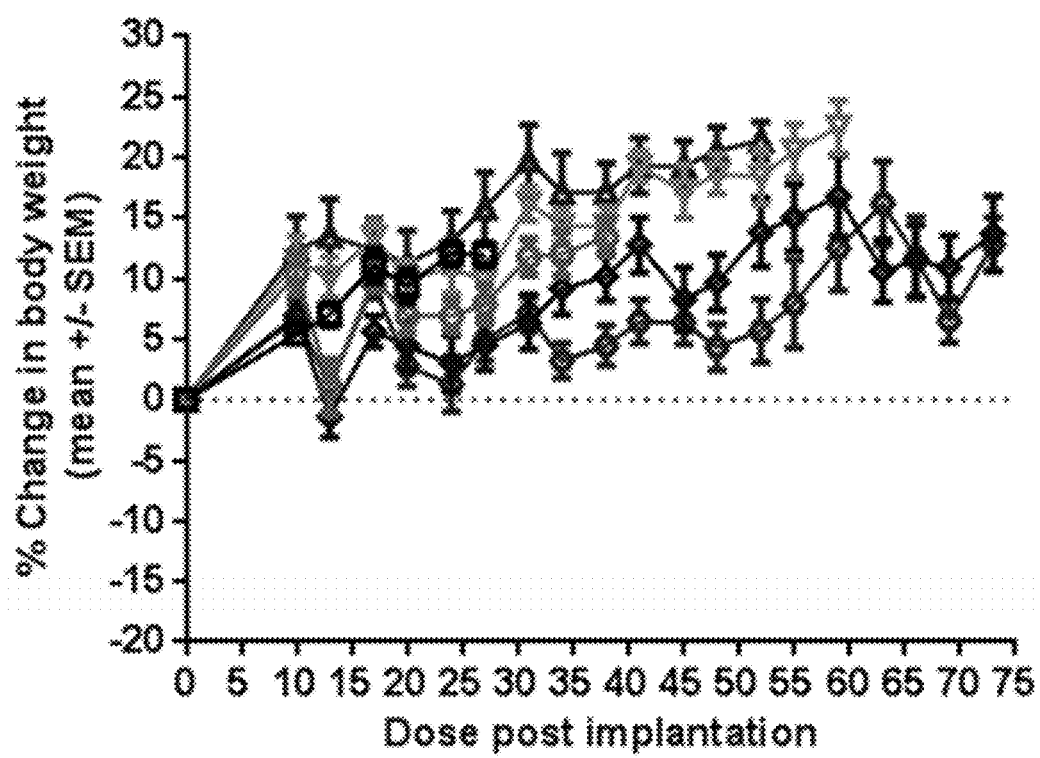
FIG. 1C—depicts tolerability of the treatments in FIG. 1A, as indicated by body weight change over time.

H727 Model:
Nude female mice tumor bearing NCI-H358, n=8 per group, were randomized into 2 groups with an average tumor volume range of 275.74 mm3. Animals were administered an oral dose of either vehicle or Compound A at 100 mg/kg daily for 14 consecutive days at a dosing volume of 10 ml/kg of animal body weight during course of treatment. Tumor volumes were measured by digital caliper 3 times a week and body weights of all animals were recorded through the course of treatment. As shown in FIGS. 1A, 1B and 1C, Compound A showed single agent activity in KRASmt NSCLC models.

In cell-based assays, Compound A has demonstrated anti-proliferative activity in cell lines that contain a variety of mutations that activate MAPK signaling. For instance, Compound A inhibited the proliferation of the non-small cell lung cancer cell line Calu-6 (KRAS Q61K), colorectal cell line HCT116 (KRAS G13D with IC50 values ranging from 0.2-1.20 µM. In vivo, treatment with Compound A generated tumor regressions in several human KRAS-mutant models including the NSCLC-derived Calu-6 (KRAS Q61K) and NCI-H358 (KRAS G12C) xenografts. In all cases, anti-tumor effects were dose-dependent and well tolerated as judged by lack of significant body weight loss. The Calu-6 model was sensitive to Compound A when implanted in both nude mice and nude rats with regressions observed at doses of 100, 200, and 300 mg/kg once daily (QD) in mice and 75 and 150 mg/kg QD in rats. Tumor stasis in this model was observed at 30 mg/kg QD and 35 mg/kg QD in mice and rats, respectively. Regressions were also achieved in a second human NSCLC model, NCI-H358, at the 200 mg/kg QD dose in mice and in the human ovarian Hey-A8 xenograft at doses as low as 30 mg/kg QD in mice. Furthermore, data from a dose fractionation efficacy study in Calu-6 xenografts demonstrated that across different dosing levels, Compound A dosed QD and fractioned twice a day (BID) showed similar levels of anti-tumor activity. These results support exploration of QD or BID dose regimen in the clinic. Collectively the in vitro and in vivo MAPK-pathway suppression and anti-proliferative activity observed for Compound A at well-tolerated doses suggests that Compound A may have anti-tumor activity in patients with tumors harboring activating lesions in the MAPK pathway and in particular may therefore be useful as a single agent or in combination with a second agent, such as an inhibitor affecting a different step of the MAPK pathway, for the treatment of NSCLC patients harboring KRAS mutations. Compound A has been shown to have activity as a single agent against various other cancers that express gain of function mutations in the MAPK pathway, e.g. in RAS or RAF, including ovarian cancer, pancreatic cancer, and melanoma, and in model systems has been shown to be more effective against these conditions when used in combination with an ERK inhibitor such as Compound B.

Example 3

Compound B is an inhibitor of ERK 1/2. The compound is disclosed and its preparation described in published PCT patent application WO2015/066188.

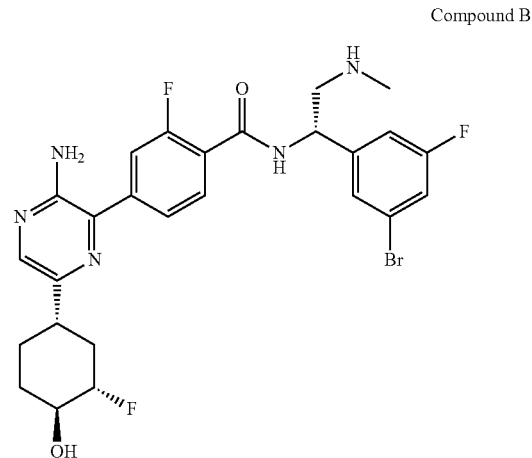 [SMILES: CNC[C@@H](NC(=O)c1ccc(-c2nc([C@H]3CC[C@H](O)[C@@H](F)C3)cnc2N)cc1F)c1cc(F)cc(Br)c1]

Compound B

In some embodiments, this compound is used as its hydrochloride salt.

In a 3 day proliferation assay, Compound B showed robust inhibition of cell growth, with IC$_{50}$ values of less than 1 µM in a subset of cell lines harboring KRAS mutations, including lung cancer cell line Calu6 (KRAS$^{Q61K}$) ovarian cancer cell line HeyA8 (KRAS$^{G12D}$), pancreatic cancer cell lines AsPC-1 (KRAS$^{G12D}$) and PSN1 (KRAS$^{G12R}$).

Example 4: Effect of a Combination of Compound a and Compound B on KRAS Mutant Cell Lines The effect on proliferation of combining Compound A and Compound B was assessed in vitro in a panel of fourteen

(14) KRAS-mutant cell lines derived from NSCLC (4), colorectal cancer (CRC) (4) and pancreatic ductal adenocarcinoma (PDAC) (6).

The CellTiter-Glo® (CTG) Luminescent Cell Viability Assay kit (Promega, Madison, WI, USA) measures the amount of ATP present in a well after lysis of the cells. The ATP released upon lysis is measured in an enzymatic reaction which includes Luciferase and its substrate Luciferin. The amount of light emitted is proportional to the amount of ATP, which in turn is proportional to the number of live cells in the well. This assay is used to determine the proportion of viable cells after drug treatment.

Reagents used for the CTG assay including the 14 cell lines, media, and cell densities are described in the Tables below.

Cells were seeded in duplicate sets according to the information in the Table below at 50 ul/well in white 384 well tissue culture plates (#3707, Corning, NY, USA). The following day, compounds were diluted in DMSO in a compound plate (#788876, Greiner, Monroe, NC, USA) creating a 7 point 1:3 dilution series (1000 times the required final concentrations). Compounds were dispensed to cell plates to achieve a 1:1000 dilution using an acoustic dispenser (ATS100, EDC Biosystems, California, USA). For example, one well of the compound plate contained 10 mM of Compound A and the transfer of 50 nL of compound into 50 uL of cells achieved a final concentration of 10 uM for that compound in that given well. Section 2.3 outlines the layout and concentrations of the combinations grid that was created in our assay plates using the ATS100. Assay plates were subsequently returned to a humidified $CO_2$ incubator at 37° C.

After 5 days of compound incubations 25 uL/well of CTG viability reagent was added to each well (75 ul total volume) and after 15 minutes of incubation at room temperature the plates were read on a microplate reader using a 0.1 second ultrasensitive luminescence protocol (Envision, Perkin Elmer, Hopkington, MA, USA).

Data was normalized to the average of the untreated wells (treated with DMSO only) for that given cell line. Values were then subtracted from 1 and multiplied by 100 to represent % Inhibition. Normalized data was then fit to curves using the four parameters logistic (4PL) regression curve fitting model by proprietary software (HELIOS). $IC_{50}$'s (half maximal inhibitory concentration) were reported for single agent curves where the compound inhibited cell growth by 50%.

TABLE

Assay Reagents and Materials
Reagent

White polystyrene tissue culture plates (384)
Black COC compound plate (384)
Roswell Park Memorial Institute (medium): (RPMI) medium:
Ham's F12 medium
McCoy's 5A medium
Eagle's minimum essential medium (EMEM)
0.05% Trypsin-EDTA
100% Fetal bovine serum (FBS)
Phosphate buffered saline
DMSO
CellTiter-Glo ® viability reagent

TABLE

Cell line media and seeding densities

| Cell Line | Mutation | Media | Cancer Type | Seeding density (384 well, 50 uL/well) |
|---|---|---|---|---|
| HCT-15 | $KRAS^{G13D}$ | RPMI + 10% FBS | CRC | 400 |
| SK-CO-1 | $KRAS^{G12V}$ | EMEM + 10% FBS | CRC | 1500 |
| HCC-56 | $KRAS^{G12V}$ | RPMI + 10% FBS | CRC | 3000 |
| HCT116 | $KRAS^{G12D}$ | McCoy's + 10% FBS | CRC | 200 |
| Calu-6 | $KRAS^{Q61K}$ | EMEM + 10% FBS | NSCLC | 1000 |
| A549 | $KRAS^{G12S}$ | F12 + 10% FBS | NSCLC | 200 |
| HCC-2108 | $KRAS^{Q61H}$ | RPMI + 10% FBS | NSCLC | 600 |
| NCI-H2122 | $KRAS^{G12C}$ | RPMI + 10% FBS | NSCLC | 800 |
| HUP-T4 | $KRAS^{G12V}$ | EMEM + 10% FBS | PDAC | 700 |
| HPAF-II | $KRAS^{G12D}$ | EMEM + 10% FBS | PDAC | 1000 |
| SU.86.86 | $KRAS^{G12D}$ | RPMI + 10% FBS | PDAC | 500 |
| CFPAC-1 | $KRAS^{G12V}$ | DMEM + 10% FBS | PDAC | 900 |
| TCC-PAN2 | $KRAS^{G12R}$ | RPMI + 10% FBS | PDAC | 1000 |
| PSN1 | $KRAS^{G12R}$ | RPMI + 10% FBS | PDAC | 200 |

In all cases combinations were assessed in a checkerboard formatted matrix using Compound A concentrations ranging from 0.014 to 10 uM and Compound B concentrations ranging from 0.011 to 8.0 uM. Whether or not the combination was synergistic in a particular cell line was determined using two measurements of synergy; synergy score and combination index (CI) at a 50 or 75 percent inhibition level (Lehar et al 2009).

Combining Compound A and Compound B was moderately to strongly synergistic in 7/14 cell lines tested. A summary of these values for each cell line is shown in the Table below.

TABLE

Summary of Compound A x Compound B Synergy Scores and $CI_{50}$ values

| Cell Line | Cancer Type | KRAS Mutation | Loewe Synergy Score | Loewe Synergy Score Error | $CI_{50}$ | $CI_{50}$ Error | Synergy Determination |
|---|---|---|---|---|---|---|---|
| HCT-15 | CRC | $KRAS^{G13D}$ | 2.89 | 0.201 | 0.50 | 0.04 | Additive/Synergy |
| SK-CO-1 | CRC | $KRAS^{G12V}$ | 2.67 | 0.135 | 0.70 | 0.14 | Additive/Synergy |
| HCC-56 | CRC | $KRAS^{G12V}$ | 2.18 | 0.29 | 0.48 | 0.12 | Synergy |
| HCT 116 | CRC | $KRAS^{G12D}$ | 2.08 | 0.15 | 0.88 | 0.09 | Additive/Synergy |
| Calu-6 | NSCLC | $KRAS^{Q61K}$ | 3.43 | 0.228 | 0.58 | 0.13 | Synergy |
| A549 | NSCLC | $KRAS^{G12S}$ | 3.05 | 0.212 | 0.60 | 0.09 | Synergy |
| HCC-2108 | NSCLC | $KRAS^{Q61H}$ | 2.62 | 0.167 | 0.59 | 0.05 | Additive/Synergy |

TABLE-continued

Summary of Compound A × Compound B Synergy Scores and $CI_{50}$ values

| Cell Line | Cancer Type | KRAS Mutation | Loewe Synergy Score | Loewe Synergy Score Error | $CI_{50}$ | $CI_{50}$ Error | Synergy Determination |
|---|---|---|---|---|---|---|---|
| NCI-H2122 | NSCLC | $KRAS^{G12C}$ | 1.62 | 1.49 | 0.83 | 2.20 | Additive |
| HUP-T4 | PDAC | $KRAS^{G12V}$ | 5.94 | 0.19 | 0.37 | 0.03 | Synergy |
| HPAF-II | PDAC | $KRAS^{G12D}$ | 4.4 | 0.202 | 0.76 | 0.07 | Synergy |
| SU.86.86 | PDAC | $KRAS^{G12D}$ | 3.3 | 0.35 | 0.22 | 0.04 | Synergy |
| CFPAC-1 | PDAC | $KRAS^{G12V}$ | 2.14 | 0.144 | 0.36 | 0.03 | Synergy |
| TCC-PAN2 | PDAC | $KRAS^{G12R}$ | 1.54 | 0.252 | 0.45 | 0.20 | Additive/Synergy |
| PSN1 | PDAC | $KRAS^{G12R}$ | 0.872 | 0.0995 | ND | ND | Additive |

A general guideline for interpretation of the scores/values is provided in the Table below.

TABLE

Interpretation of combination activity

| Combination parameters | Effect description |
|---|---|
| SS > 3.0 and Best C.I. > 0.5 | Synergy |
| SS > 2.0 and Best C.I. < 0.5 | Synergy |
| SS > 2.0 and Best C.I. > 0.5 | Additive/Synergy |
| SS > 1.0 but < 2.0 and Best C.I. < 0.5 | Additive/Synergy |
| SS < 1.0 and Best C.I. < 0.5 | Additive |

Within the set of cell lines tested synergy was predominantly observed in models derived from NSCLC and PDAC lineages, with the Calu-6 ($KRAS^{Q61K}$) and HUPT4 ($KRAS^{G12V}$) models being the most responsive for the two lineages, respectively.

Example 5: Compound a in Combination with Compound B in a Xenograft Model of Disease Calu-6 NSCLC tumors were established in athymic female mice by subcutaneous injection of 10 million cells in 50% Matrigel™ into the flank of each mouse. When tumors reached approximately 250 mm3, mice were randomized according to tumor volume into treatment groups (n=7). Test agents were administered orally once daily (qd) or once every other day (q2d) at the dose levels indicated. A-B) Tumor volumes of treatment groups vs. days post randomization. C) Mean percent change in body weight from initial. Data for these treatments are shown in FIGS. 1A, 1B and 1C.

Combined treatment with Compound A and Compound B led to increased depth and durability of tumor response compared to either single agent in the human NSCLC xenograft Calu-6. Compound A dosed at 30 mg/kg qd achieved 26% T/C, while Compound B dosed at either 75 mg/kg q2d or 50 mg/kg qd achieved 4% T/C, and 22% regressions, respectively, 17 days post dosing. Combining Compound A dosed at 30 mg/kg qd with Compound B dosed at either 50 mg/kg qd or 75 mg/kg q2d achieved 66% and 51% regressions, respectively, 17 days post dosing. In addition to the increased depth of response, the combination of Compound A and Compound B also led to an increased durability of response. While tumors in mice dosed with single agents Compound A and Compound B progressed under treatment, the combination of Compound A and Compound B together (regardless of dose of Compound B) maintained tumor regressions 42 days post dosing. Collectively, these data suggest that combined treatment with Compound A and Compound B may achieve greater and more durable responses in patients with activated MAPK pathway due to gain-of-function mutations in the MAPK pathway. Furthermore, these results support the potential exploration of intermittent dosing of Compound B when combined with Compound A. The tested combinations were well tolerated as judged by lack of body weight loss.

Example 6: A Phase I Dose Finding Study of Compound a in Adult Patients with Advanced Solid Tumors Harboring MAPK Pathway Alterations Alone or with Compound B Compound A as Single Agent The recommended starting dose and regimen of Compound A single agent in this study is 100 mg QD orally based on the preclinical safety, tolerability data, PK/PD data obtained in preclinical studies, as well as exploratory human efficacious dose range projection. Starting doses of 100 mg, 200 mg, 250 mg, 300 mg, or 400 mg may be used; preliminary data suggesting a starting dose of 250 mg once daily may be effective on solid tumors. For maximum flexibility of dosing, Compound A may be prepared as 50 mg and/or 100 mg tablets for oral administration. A proposed formulation for clinical use of Compound A includes Compound A combined with one or more excipients selected from hydroxypropylmethylcellulose (Hypromellose), colloidal silicon dioxide, microcrystalline cellulose, polyvinylpyrrolidone (Povidone), and magnesium stearate, and can be prepared in the form of tablets for oral administration, suitably containing 50 mg or 100 mg of Compound A.

Provisional doses for dose escalation can be found in the Table below.

TABLE

Provisional dose levels for Compound A

| Dose level (DL) | Proposed daily dose* | Increment from previous dose |
|---|---|---|
| −1** | 50 mg | −50% |
| 1 (starting dose) | 100 mg | (starting dose) |
| 2 | 200 mg | 100% |
| 3 | 400 mg | 100% |
| 4 | 800 mg | 100% |
| 5 | 1200 mg | 50% |

*It is possible for additional and/or intermediate dose levels to be added during the course of the study, including doses outside the range of provisional doses shown in this table.
**Dose level −1 represent treatment doses for patients requiring a dose reduction from the starting dose level.

In the dose expansion part, patients in Compound A single agent arm are treated with Compound A at the recommended dose and regimen selected based on the dose escalation data. This dose is expected to be safe and tolerated in adult patients in all indications included in the trial.

The clinical regimen for this first-in-human trial is a continuous once daily dosing schedule for Compound A. The QD regimen has been demonstrated to be efficacious and tolerated in preclinical studies. In Calu6 xenografts, similar levels of efficacy were achieved with either QD or fractionated BID regimens, suggesting efficacy is related to overall exposure. The predicted human PK and the predicted half-life (~9 h), also suggest efficacious exposure can be achieved with QD dosing.

In addition, an efficacious dosage can be determined by monitoring biomarkers indicative of MAP kinase pathway inhibition. In particular, DUSP6 (dual specificity phosphatase 6) is a known biomarker for this pathway, and in vivo levels of DUSP6 have been shown to drop in a subject receiving a dosage of Compound A that is associated with efficacious plasma levels of Compound A. Thus DUSP6 may be used as a pharmacodynamics biomarker in subjects treated with Compound A, whether as a single agent or as a combination with another therapeutic agent.

Compound A in Combination with Compound B

Compound B can be used as its hydrochloride salt. For testing purposes, it may be administered orally, either formulated with one or more excipients or as the compound alone, contained in a pharmaceutically acceptable capsule such as a soft or hard gel cap or admixed with a convenient medium for administration by gavage.

The dose escalation of Compound A in combination with Compound B began with a dosing regimen identified for Compound A as a single agent: the starting dose of Compound A was lower than the single agent dose. The selection of this dose thus should minimize exposure to potentially toxic drug levels while limiting the number of patients that might receive doses too low to provide good efficacy.

The regimen for Compound A was the same as selected for single agent Compound A. In case both regimens for Compound A single agent will be explored during single agent expansion part, then one preferred regimen will be chosen for the combination based on all available data including safety and exposure. Switching Compound A dose regimen in the combination arm at a later stage may be decided based on emerging data.

Compound B was administered at a dosage level projected to provide exposure sufficient to provide effective tumor suppression based on activity in preclinical models. Based on preclinical testing, efficacy appears to be driven by time above an effective plasma level, thus dosing can be determined in one embodiment by monitoring plasma levels of Compound B. It is projected that the desired trough plasma level for efficacy is about 600 nM, or about 350 ng/mL; accordingly, the dosage and administration schedule (frequency) can be guided by the goal of maintaining a plasma concentration of Compound B above this trough plasma level for at least a day, or at least a week, or for a treatment cycle such as 1, 2, 3, or 4 weeks as judged appropriate by the treating physician.

The clinical regimen for this trial was a continuous once daily dosing schedule for Compound A and Compound B.

This was further confirmed by preliminary results obtained from the clinical trial. A subject with non-small cell lung cancer (NSCLC) treated with 1200 mg QD of Compound A was shown to result in partial response of −35% according to the Response Evaluation Criteria In Solid Tumors (RECIST) criteria.

In the dose expansion part, patients in the combination arm are treated at the recommended dose and regimen for the drug combination based on the dose escalation data. In order to provide suitable dosing flexibility, Compound B may be prepared in the form of gel caps containing various amounts of Compound B (optionally as its hydrochloride) such as doses of about 5 mg, 20 mg, 50 mg, or 100 mg per gelcap.

Patients in the combination arm may be treated with Compound A at a daily dose of about 100 mg, or about 150 mg, or about 200 mg, or about 250 mg and with Compound B at a daily dose of about 50 mg, or about 75 mg, or about 100 mg. For example, patients may be administered a total dose of about 100 mg Compound A daily and a total dose of about 100 mg Compound B daily, the doses being preferably administered once a day. Patients may also receive a total dose of about 200 mg Compound A daily and a total dose of about 100 mg Compound B daily, the doses being preferably administered once a day.

Patients receiving the combination therapy include NSCLC patients, e.g. adult patients, with advanced or metastatic KRAS-mutant or BRAF mutant (e.g. BRAF V600E-mutant) NSCLC.

These patients may have progressed following standard of care or for whom no effective standard therapy exists.

The efficacy of the trial may be evaluated measuring overall response rate (ORR), disease control rate (DCR), duration of response (DOR), progression free survival (PFS) as per RECIST version 1.1 and overall survival (OS).

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed:

1. A method for treating a cancer, selected from BRAF-mutant NSCLC and NSCLC and KRAS-mutant ovarian cancer, in a subject in need thereof comprising administering to the subject a therapeutically effective amount of the pharmaceutical combination of: (i) a CRAF inhibitor which is Compound A,

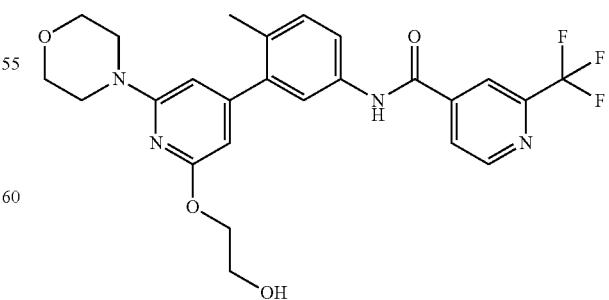

or a pharmaceutically acceptable salt thereof; and (ii) an ERK inhibitor which is Compound B,

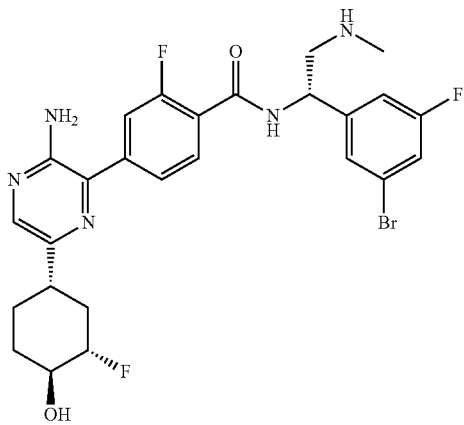 [SMILES: CNC[C@@H](NC(=O)c1ccc(-c2nc([C@H]3CC[C@H](O)[C@@H](F)C3)cnc2N)cc1F)c1cc(F)cc(Br)c1]

or a pharmaceutically acceptable salt thereof.

2. The method of claim 1, wherein the CRAF inhibitor, or a pharmaceutically acceptable salt thereof, and the ERK inhibitor, or a pharmaceutically acceptable salt thereof, are administered separately, simultaneously or sequentially.

3. The method according to claim 2 wherein the cancer expresses at least one mutation selected from the group consisting of RAF mutations V600E, V600D, and G464E, and RAS mutations A146T and Q61L.

4. The method according to claim 3 wherein the CRAF kinase inhibitor, or a pharmaceutically acceptable salt thereof, is administered at a daily dose of about 100 mg, or about 150 mg, or about 200 mg, or about 250 mg.

5. The method according to claim 4, wherein the ERK inhibitor, or a pharmaceutically acceptable salt thereof, is administered at a dose of about 50 mg per day, or about 75 mg per day, or about 100 mg per day.

6. The method according to claim 1, wherein Compound A is administered at a daily dose of 100 mg and Compound B is administered at a daily dose of 100 mg.

7. The method according to claim 1, wherein Compound A is administered at a daily dose of 200 mg and Compound B is administered at a daily dose of 100 mg.

8. A combined preparation comprising (a) one or more dosage units of a CRAF inhibitor according to claim 1, or a pharmaceutically acceptable salt thereof, and (b) one or more dosage units of an ERK inhibitor according to claim 1, or a pharmaceutically acceptable salt thereof, and at least one pharmaceutically acceptable carrier.

\* \* \* \* \*